United States Patent
Rangachari et al.

(10) Patent No.: US 7,705,178 B2
(45) Date of Patent: Apr. 27, 2010

(54) ALTERING THE CRYSTAL SIZE DISTRIBUTION OF N-(PHOSPHONOMETHYL) IMINODIACETIC ACID FOR IMPROVED FILTRATION AND PRODUCT QUALITY

(75) Inventors: Sunder S. Rangachari, Ballwin, MO (US); Todd C. Friedman, Imperial, MO (US); Sherrol Lee Baysdon, Lonedell, MO (US); David Z. Becher, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 798 days.

(21) Appl. No.: 11/411,192

(22) Filed: Apr. 25, 2006

(65) Prior Publication Data

US 2006/0247463 A1 Nov. 2, 2006

Related U.S. Application Data

(60) Provisional application No. 60/674,644, filed on Apr. 25, 2005.

(51) Int. Cl.
C07F 9/30 (2006.01)
(52) U.S. Cl. ...................................................... 562/17
(58) Field of Classification Search ........................ None
See application file for complete search history.

(56) References Cited

U.S. PATENT DOCUMENTS

| | | | |
|---|---|---|---|
| 3,950,402 A * | 4/1976 | Franz | 562/17 |
| 4,299,978 A | 11/1981 | Nakayasu et al. | |
| 4,357,172 A | 11/1982 | Edwards | |
| 4,618,429 A | 10/1986 | Herrigel | |
| 4,657,705 A | 4/1987 | Miller et al. | |
| 4,724,103 A | 2/1988 | Gentilcore | |
| 4,775,498 A | 10/1988 | Gentilcore | |
| 4,831,185 A | 5/1989 | Chan et al. | |
| 5,011,988 A | 4/1991 | Thunberg | |
| 5,041,627 A | 8/1991 | Baysdon et al. | |
| 5,047,088 A | 9/1991 | Liaw et al. | |
| 5,312,972 A | 5/1994 | Cullen | |
| 5,338,530 A | 8/1994 | Thunberg | |
| 5,527,953 A | 6/1996 | Jones et al. | |
| 5,602,276 A | 2/1997 | Stern et al. | |
| 5,688,994 A | 11/1997 | Baysdon et al. | |
| 5,703,273 A | 12/1997 | Stern et al. | |
| 5,986,128 A | 11/1999 | Smith | |
| 6,113,866 A | 9/2000 | Lee et al. | |
| 6,118,022 A | 9/2000 | Cullen | |
| 6,130,351 A | 10/2000 | Stern et al. | |
| 6,515,168 B1 | 2/2003 | Parker | |
| 6,645,461 B1 | 11/2003 | Unger et al. | |
| 7,084,298 B2 | 8/2006 | Maase et al. | |

FOREIGN PATENT DOCUMENTS

| | | |
|---|---|---|
| DE | 19707994 | 9/1998 |
| DE | 19914375 | 10/2000 |
| EP | 0164923 A2 | 12/1985 |
| EP | 0425131 | 5/1991 |
| GB | 1191635 | 5/1970 |
| GB | 1575469 | 9/1980 |
| WO | 9415939 | 7/1994 |
| WO | 0014093 A1 | 3/2000 |
| WO | 0059915 | 10/2000 |

OTHER PUBLICATIONS

International Search Report and Written Opinion for Application No. PCT/US2006/015765.
Doki et al., "Product Crystal Size Distribution of Potassium Alum in Seeded Batch Cooling Crystallization Under Different Cooling Modes," Institution of Chemical Engineers, 1999, pp. 1-15, Rugby, UK.
Tahti et al., "On-Line Measurement of Crystal Size Distribution During Batch Crystallization," Institution of Chemical Engineers, 1999, pp. 1-9, Rugby, UK.
Jagadesh et al., "Seeding Effect on Batch Crystallization of Potassium Sulfate Under Natural Cooling Mode and a Simple Design Method of Crystallizer," Journal of Chemical Engineering, 1999, pp. 514-520, vol. 32, No. 4, Japan.
Chung et al., "Optimal Seeding in Batch Crystallization," The Canadian Journal of Chemical Engineering, Jun. 1999, pp. 590-596, vol. 77, No. 3, Canada.
Kohl et al., "Why is Seeding of Organic Substances in the Batch-Crystallization Still Treated as an Art?" Fr., Crystal Growth Organic Material 4th International Workshop, 1997, pp. 175-181, Shaker Verlag, Aachen, Germany.
Matthews et al., "Batch Crystallization of a Photochemical: Modeling, Control, and Filtration," American Institute of Chemical Engineers Journal, May 1998, pp. 1119-1127, vol. 44, No. 5, United States.

(Continued)

*Primary Examiner*—Daniel M Sullivan
*Assistant Examiner*—Yevegeny Valenrod
(74) *Attorney, Agent, or Firm*—Senniger Powers LLP; Joseph A. Schaper

(57) ABSTRACT

Improved processes for preparing and crystallizing N-(phosphonomethyl)iminodiacetic acid are provided. The processes include adding N-(phosphonomethyl)iminodiacetic acid seed crystals to N-(phosphonomethyl)iminodiacetic acid reaction solutions. Provided are beds of crystallized N-(phosphonomethyl)iminodiacetic acid having improved permeability and filtration rate and reduced impurities.

66 Claims, 5 Drawing Sheets

OTHER PUBLICATIONS

Jagadesh et al., "Large and Mono-Sized Product Crystals from Natural Cooling Mode Batch Crystallizer," Journal of Chemical Engineering of Japan, 1996, pp. 865-873, vol. 29, No. 5, Japan.

Liszi et al., "Crystal Growth of (E)-2-Butenedioic Acid from Aqueous Solution in Batch-Cooling Crystallization," Journal of Crystal Growth, 1996, pp. 179-182, vol. 166, Elsevier Science, North-Holland.

Tai et al., "Determination of Secondary Nucleation Kinetics Using a Batch Crystallizer," Journal of the Chinese Institute of Chemical Engineers, 1991, pp. 231-240, vol. 22, No. 4, Taiwan.

Kotaki et al., "Reactive Crystallization of Calcium Carbonate in a Batch Crystallizer," Journal of Crystal Growth, 1990, pp. 1092-1097, vol. 99, Elsevier Science, North-Holland.

Wey et al., "Analysis of Batch Crystallization Processes," Chemical Engineering Communication, 1985, vol. 35(1-6), pp. 231-252, Gordon and Breach Science Publishers, Inc. and OPA ltd., United States.

Rousseau et al., "The Influence of Seed Crystal Size on Nucleation Rates," American Institute of Chemical Engineers Journal, 1976, pp. 48-52, vol. 72, No. 153, United States.

Karpinski et al., Ch. 6, Precipitation Processes, Handbook of Industrial Crystallization, 2nd Ed., 2002, p. 141, Butterworth-Heinemann.

Tavare, Narayan S., Ch. 5., Batch Crystallizer, Industrial Crystallization: Process Simulation Analysis and Design, 1995, pp. 118-119, Plenum Press.

\* cited by examiner

ALTERING THE CRYSTAL SIZE DISTRIBUTION OF N-(PHOSPHONOMETHYL) IMINODIACETIC ACID FOR IMPROVED FILTRATION AND PRODUCT QUALITY

This application claims the benefit of U.S. provisional application Ser. No. 60/674,644, filed Apr. 25, 2005, the entire contents of which are incorporated herein by reference.

FIELD OF THE INVENTION

The present invention generally relates to improved processes for the preparation of N-(phosphonomethyl)iminodiacetic acid product of the formula (I):

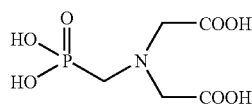

wherein the particle size is controlled to improve product quality and optimize separation efficiency of the solid product from the reaction system.

BACKGROUND OF THE INVENTION

N-(phosphonomethyl)glycine (known in the agricultural chemical art as glyphosate) and its salts are conveniently applied as a post-emergent herbicide in aqueous formulations. These compositions are highly effective and commercially important broad-spectrum herbicides useful in killing or controlling the growth of a wide variety of plants, including germinating seeds, emerging seedlings, maturing and established woody and herbaceous vegetation, and aquatic plants.

One of the more widely accepted methods of making N-(phosphonomethyl)glycine compounds comprises the liquid phase oxidative cleavage of a carboxymethyl substituent from an N-(phosphonomethyl)iminodiacetic acid ("PMIDA") substrate using an oxygen-containing gas in the presence of a heterogenous oxidation catalyst. For example, N-(phosphonomethyl)glycine may be prepared by the liquid phase oxidative cleavage of N-(phosphonomethyl)iminodiacetic acid ("PMIDA") with oxygen in accordance with the following reaction sequence:

Processes for the preparation of N-(phosphonomethyl)iminodiacetic acid are well known in the art. For example, U.S. Pat. Nos. 4,724,103 and 4,775,498 to Gentilcore, incorporated by reference herein, describe a commercially useful process for making PMIDA from an aqueous solution of an alkali metal salt of iminodiacetic acid (e.g., the disodium salt or "DSIDA"), a strong mineral acid, a source of phosphorous acid and a source of formaldehyde. In a first step, a strong acid salt of iminodiacetic acid ("IDA") is formed by reacting the DSIDA with aqueous HCl. In a subsequent phosphonomethylation ("PM") step, the IDA acid salt is reacted with phosphorous acid and formaldehyde to form PMIDA. PMIDA concentration in the reaction solution increases as the reaction proceeds and eventually a highly supersaturated solution is formed. Before formaldehyde addition is complete, a PMIDA supersaturation critical point is reached resulting in a crystallization event that is sudden, violent and nearly instantaneous thereby causing PMIDA to "crash" from solution. Formaldehyde addition and PMIDA generation continues after initial crystallization in a dynamic system of concurrent PMIDA generation and crystallization. Reaction by-products and impurities include, for example, N,N-bis-(phosphonomethyl) glycine ("glyphosine"), glycine, N-methyl-N-(phosphonomethyl)glycine ("NMG"), N-methyl-iminodiacetic acid ("N-methyl IDA"), iminodiacetic acid, unreacted formaldehyde, and the sodium-acid anion salt (e.g., NaCl). Gentilcore teaches that the PMIDA process may be optimized by splitting the total DSIDA charge between the hydrolysis and PM steps thereby converting only that portion of DSIDA added to the hydrolysis reactor to the IDA acid salt. The remainder of the DSIDA is added along with the formaldehyde to the PM reactor. The DSIDA added during the PM step is converted to IDA acid salt in situ by HCl released upon consumption of IDA.HCL in the phosphonomethylation reaction and any free HCl remaining in solution thereby minimizing the amount of acid that it is necessary in either the hydrolysis or the phosphonomethylation steps to prevent generating significant or excessive amounts of N-methyl-iminodiacetic acid by-product. By using HCl more efficiently, by-product containing less sodium chloride (NaCl) is generated, thereby producing a purer product and requiring less water to solubilize the NaCl.

U.S. Pat. No. 5,688,994 to Baysdon et al., also incorporated by reference herein, describes a process for preparing PMIDA from a source of IDA wherein the formaldehyde source and source of phosphorous acid are simultaneously infused into the reaction mixture. PMIDA is precipitated from the reaction mixture by cooling or pH adjustment. Disadvantageously, crystallization by cooling results in protracted processing time with an associated inefficient use of process equipment at the expense of decreased throughput.

The prior art processes are complicated by the necessity of removing the sodium-acid anion salt from the PMIDA product. Where the acid is HCl and the salt is NaCl, a significant portion of the NaCl is present in the PMIDA product slurry as a solid. Sodium chloride has low solubility in the presence of HCl due to the common ion effect, while PMIDA is readily soluble in the presence of HCl. By contrast, PMIDA has a low solubility in water under neutral conditions, while NaCl is readily soluble. Thus, salt removal requires that the NaCl be dissolved in the reaction solution after the formation of PMIDA is complete. Dissolution is done by adding a dilute base, such as sodium hydroxide, to the reaction mixture so that the pH is adjusted to the point at which NaCl is soluble. Adding additional water ensures that most of the NaCl is solubilized. The pH at which NaCl is readily soluble generally corresponds to the PMIDA isoelectric point, i.e., the point of minimum PMIDA solubility. Thus, upon pH adjustment conditions are most favorable for PMIDA crystallization. Crystallized PMIDA can then be isolated from the mixture by solid-liquid separation means known to those of skill in the art such as, for example, filtration or centrifugation. Isolated PMIDA may then be washed to remove residual NaCl and other impurities, and dried.

PMIDA crystallization in processes known in the art may be generalized as follows. First, rapid crashing of PMIDA from solution results in a large number of relatively small crystals that tend to form dense packed beds in solid liquid separation equipment thereby exhibiting low permeability and liquid removal capability resulting in protracted processing times and associated process bottlenecking and incomplete impurity removal. Second, rapid crystallization may increase occluded (i.e., included or "trapped") impurity rich mother liquor in the crystalline structure, which is difficult to remove in the PMIDA isolation and washing steps. Third, the relatively large volume of water required to solubilize NaCl may lead to an increased loss of PMIDA in the mother liquor and also result in waste volume increase. Moreover, the large volume further contributes to solid-liquid separation equipment bottlenecking issues.

Generally, a high degree of supersaturation driving force is necessary to initiate crystal nucleation. In various crystallization systems, seeding of saturated solutions is known for initiating crystallization, and in both saturated and non-saturated systems seeding may be used to provide sites for accretion of crystals and to regulate crystal growth. For example, where product is to be crystallized from a reaction solution, the solution may typically be cooled or its pH adjusted to establish supersaturation and, thus, generate a driving force for crystallization. In various known systems, seed crystals may be added prior or subsequent to the adjustment which establishes supersaturation. See, e.g., Liaw U.S. Pat. No. 5,047,088. One of skill in the art will recognize that seed crystals can be added to a non-supersaturated solution in order to provide a site for material crystallization. It is well known to those skilled in the art that following the completion of a product-generation reaction, seed crystals may be added to the non-supersaturated product solution followed by, for example, pH adjustment or cooling at a predetermined rate in order to generate and maintain a sufficient level of supersaturation, thus driving force for product crystallization. In those methods supersaturation is induced, for example, by solubility reduction via pH adjustment or cooling, but not dynamically by product generation via chemical reaction. See generally U.S. Pat. No. 5,047,088 to Liaw. The prior art does not describe seeding dynamic systems wherein product generation and crystallization occur simultaneously.

One of skill in the art will also recognize that rapid induction of a high degree of supersaturation in the absence of seed crystals can result in instantaneous, uncontrolled, nucleation and crystallization with limited post-nucleation crystal growth. Such crystals are typically small with high impurity inclusion. Generally, generation of high supersaturation is done by instantaneously reducing solubility, for example by pH adjustment to the solute isoelectric point, addition of a solvent in which the solute exhibits low solubility, or rapid temperature reduction by "flash crystallization."

The prior art provides little teaching regarding controlling particle size and particle size distribution in dynamic processes in which product generation and crystallization from solution occur concurrently. In such systems supersaturation is induced by reaction rather than by solubility reduction through, for example, pH adjustment or temperature change. Likewise, little guidance is provided in the art for controlling crystal growth rate in such dynamic systems.

U.S. Pat. Nos. 5,011,988 and 5,338,530 to Thunberg describe the crystallization of iminotriacetic acid ($N(CH_2COOH)_3$ or "NTA") from a mother liquor solution containing about 2.9% NTA, 6.3% IDA and 22.6% $Na_2SO_4$. The mother liquor pH is adjusted to the NTA isoelectric point of about 2.1 followed by NTA seeding to initiate crystallization. Notably the initial concentration of NTA is low; thus, high degrees of supersaturation are never achieved.

Although PMIDA processes known in the art are of significant utility, a need persists for improvements that might further reduce product cost, increase product purity and throughput, and reduce environmental impact. A significant advancement over the prior art could be achieved by developing a high throughput process whereby PMIDA crystallization is controlled to yield product characterized by crystals having a low degree of impurity inclusion, and having a large, uniform and porous crystalline morphology. Moreover, the crystals should be capable of forming a uniform, substantially porous bed in solid-liquid separation equipment and exhibit a high dewatering rate thereby maximizing the effectiveness of removing impurities by washing, and material throughput. It would be a further advancement if the crystals could be quickly prepared in a controlled manner by, for example, crashing from solution or flash crystallization thereby obviating the need for protracted rate controlled crystallization cooling cycles.

SUMMARY OF THE INVENTION

The present invention provides improved processes for preparing and crystallizing N-(phosphonomethyl)iminodiacetic acid. Also provided are beds of crystallized N-(phosphonomethyl)iminodiacetic acid having improved permeability and filtration rate.

One embodiment of the present invention is directed to a process for the crystallization of N-(phosphonomethyl)iminodiacetic acid from a reaction solution comprising N-(phosphonomethyl)iminodiacetic acid. The process comprises adding N-(phosphonomethyl)iminodiacetic acid seed crystals to the reaction solution and forming a bed comprising crystallized N-(phosphonomethyl)iminodiacetic acid.

Another embodiment is directed to a process for preparing and crystallizing N-(phosphonomethyl)iminodiacetic acid. The process comprises combining an alkali metal salt of iminodiacetic acid, a strong mineral acid, a source of phosphorous acid and a source of formaldehyde to form a reaction solution comprising N-(phosphonomethyl)iminodiacetic acid. N-(phosphonomethyl)iminodiacetic acid seed crystals are added to the reaction solution and a degree of saturation in the reaction solution is induced sufficient to cause crystallization of N-(phosphonomethyl)iminodiacetic acid onto the seed crystals by reacting components of the reaction solution to increase the concentration of N-(phosphonomethyl)iminodiacetic acid.

Another embodiment is directed to a process for preparing and crystallizing N-(phosphonomethyl)iminodiacetic acid under agitation. The process comprises combining reaction components including an alkali metal salt of iminodiacetic acid, a strong mineral acid, a source of phosphorous acid and a source of formaldehyde to form a reaction solution. The components of the reaction solution are agitated and reacted to produce N-(phosphonomethyl)iminodiacetic acid and form a bed comprising N-(phosphonomethyl)iminodiacetic acid crystals. The agitation rate is selected to provide a bed of crystallized N-(phosphonomethyl)iminodiacetic acid having a permeability of at least about $1 \times 10^{-9}$ cm$^2$, the permeability being greater than a bed of crystallized N-(phosphonomethyl)iminodiacetic acid crystals prepared by an otherwise identical process at a higher agitation rate.

Another embodiment of a process for preparing and crystallizing N-(phosphonomethyl)iminodiacetic acid comprises combining an alkali metal salt of iminodiacetic acid, a strong mineral acid, a source of phosphorous acid and a source of formaldehyde to form a phosphonomethylation reaction solution comprising N-(phosphonomethyl)iminodiacetic acid. The source of formaldehyde is added to the phosphonomethylation reaction solution according to an addition schedule comprising (i) adding a first portion of the source of formaldehyde; (ii) interrupting the addition of the source of formaldehyde; and (iii) adding a second portion of the source of formaldehyde. The addition schedule causes supersaturation of N-(phosphonomethyl)iminodiacetic acid in the reaction solution and crystallization of the N-(phosphonomethyl)iminodiacetic acid.

The present invention is further directed to a bed comprising N-(phosphonomethyl)iminodiacetic acid crystals, water and sodium chloride. The bed has a permeability of at least about $1 \times 10^{-9}$ cm$^2$ and a modified filtration rate of at least about 5 mL·cm/min.

The present invention is further directed generally to a process for preparing and crystallizing a product. The process comprises combining one or more product precursor compounds to form a reaction solution and reacting the product precursor compound or compounds to form the product. Seed crystals of the product are added to the reaction solution and a degree of saturation in the reaction solution is induced sufficient to cause crystallization of the product onto the seed crystals by chemical reaction that comprises reacting the product precursor compound or compounds to increase the concentration of the product in the reaction solution.

DETAILED DESCRIPTION OF THE PREFERRED EMBODIMENTS

Figure 1:
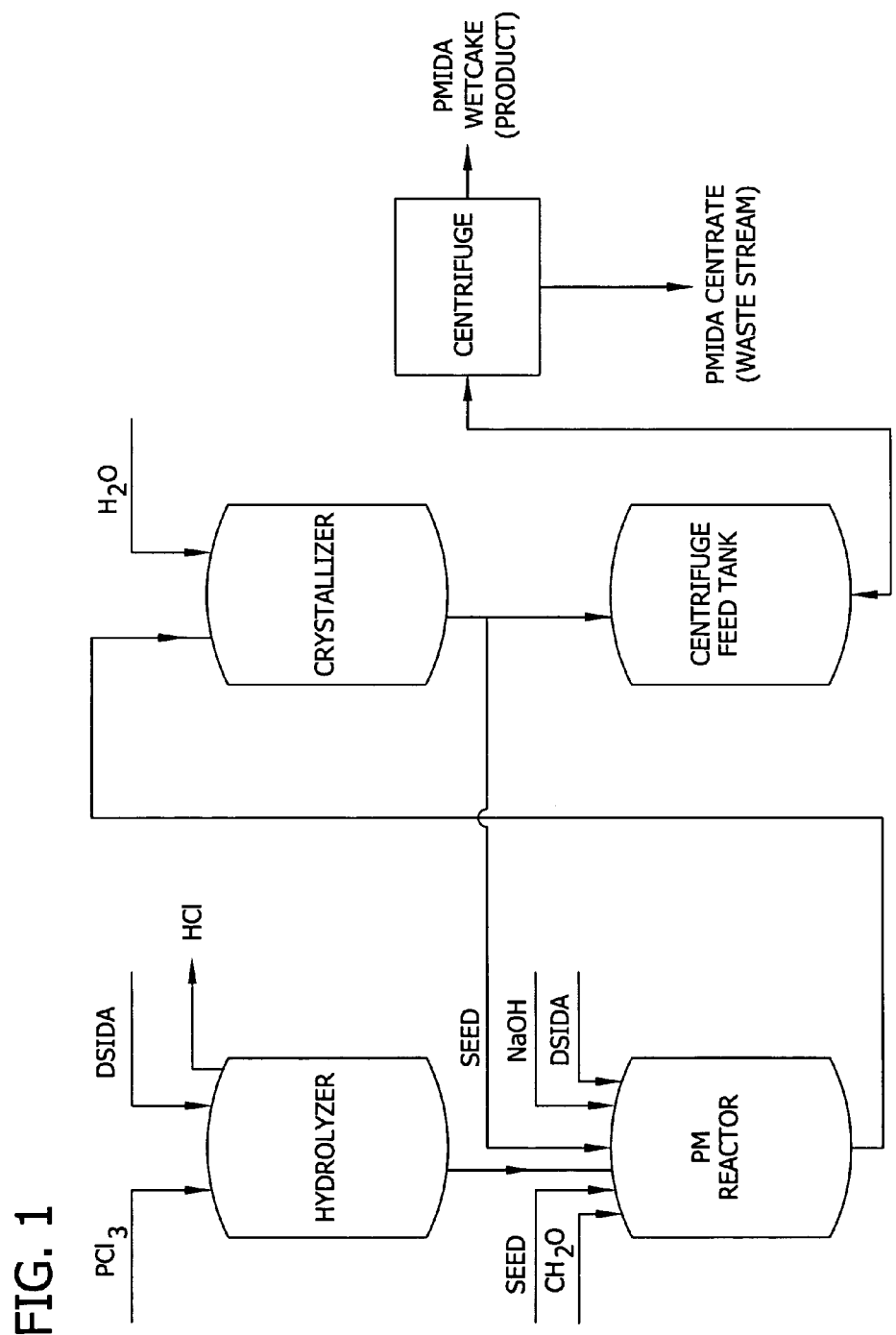
FIG. 1 schematically illustrates prior art processes for the preparation of N-(phosphonomethyl)iminodiacetic acid ("PMIDA") as well as seed crystal introduction points for practicing the present invention.

In the preparation of PMIDA by the addition of formaldehyde to a strong acid salt of IDA in an aqueous system containing phosphorous acid, a critical supersaturated concentration of PMIDA is reached prior to the point at which a stoichiometric quantity of formaldehyde has been added wherein a sudden, violent and nearly instantaneous nucleation and crystallization event causes PMIDA to crash from solution in a generally uncontrolled manner as crystals which may be characterized as having fine particle size and having significant inclusion of mother liquor and impurities. Further, in some instances the crystals may form tightly packed beds in solid/liquid separation equipment that are difficult to dewater and wash.

In accordance with the present invention, it has been discovered that PMIDA crystal size and distribution, structure, and quantity of included impurities may be controlled by seeding the PM reaction mixture prior to the time that the critical supersaturation concentration of PMIDA is reached.

It has further been discovered that crystal size and crystal purity may be individually controlled by selective seeding at certain points during the progression of the PMIDA generation reaction sequence. The present invention has particular applicability to the optimization of cycle time, PMIDA purity and PMIDA yield requirements in order to maximize process equipment utilization, minimize PMIDA product cost and minimize associated environmental burden. In particular, it is now disclosed that seeding at a low to moderate degree of supersaturation enables controlled PMIDA crystal growth, and produces crystals containing low included impurities. Moreover, analysis of the particle size distribution of the inventive crystals indicates a generally more narrow particle size distribution around the mean particle size as compared to crystal size distributions known in the art. The result is a reduced ratio of small crystals, or fines, to the mean particle size than crystals described in the art. The inventive PMIDA crystals form beds in solid/liquid separation equipment that exhibit improved porosity, dewatering and washing properties over that which is known in the art. It is further disclosed that seeding at a moderate to high degree of supersaturation generates PMIDA crystals having low levels of included impurities and having even a smaller ratio of fines to the mean particle size resulting in markedly improved porosity, dewatering and washing properties over PMIDA crystals described in the art.

PMIDA Preparation

The prior art describes numerous processes for the preparation of PMIDA. See for example U.S. Pat. No. 4,724,103 and U.S. Pat. No. 4,775,498 to Gentilcore, U.S. Pat. No. 5,688,994 to Baysdon et al., U.S. Pat. No. 5,986,128 to Smith and U.S. Pat. No. 6,130,351 to Stern, et al., all of which are incorporated by reference.

U.S. Pat. No. 4,724,103, generally described above, teaches a three step process for the preparation of PMIDA according to the following overall reaction:

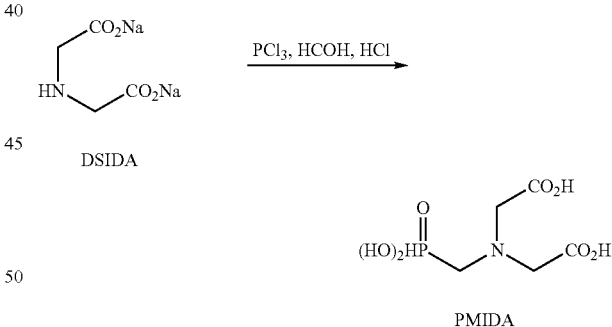

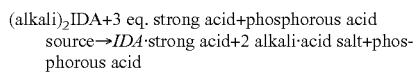

In the first step, an alkali salt of IDA, a strong mineral acid and a source of phosphorous acid are reacted in an aqueous media in a hydrolyzer to form a mixture containing the strong mineral acid salt of IDA and phosphorous acid according to the following general equation:

(alkali)$_2$IDA+3 eq. strong acid+phosphorous acid source→IDA·strong acid+2 alkali·acid salt+phosphorous acid The disodium salt of IDA is preferred. The strong acid should have a pKa less than phosphorous acid. Suitable strong acids include, for example, sulfuric, hydrobromic, hydroiodic and hydrochloric. Hydrochloric acid is preferred. Phosphorous acid can be added or can be generated in situ by the hydrolysis of $PCl_3$ in the aqueous solution to phosphorous acid and hydrochloric acid.

Preferably, the phosphorous acid source is phosphorus trichloride, the strong acid is hydrochloric that is generated primarily or exclusively in situ, and the IDA is in the form of the disodium salt (DSIDA). In such embodiments, $PCl_3$ is hydrolyzed to phosphorous acid ($H_3PO_3$) and HCl along with the simultaneous neutralization of $Na_2IDA$ to iminodiacetic acid hydrochloride (IDA.HCL) and NaCl according to the following equation:

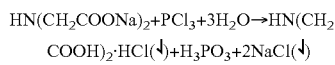

In these embodiments, the phosphorus trichloride is hydrolyzed to phosphorus acid in the $Na_2IDA$ solution. HCl, which results from hydrolysis of phosphorous trichloride, acidifies the $Na_2IDA$ to afford the hydrochloride salt and NaCl. Because the reaction is preferably conducted at a temperature in excess of 100° C., water vapor and a fraction of the HCl may be evolved from the reaction mixture and recovered in a hydrolysis reactor condenser. Optionally, a fraction of HCl driven from the reaction may be recycled to a subsequent batch. The IDA hydrochloride salt and NaCl are both substantially insoluble and form a slurry in an aqueous solution which is saturated with HCl.

To maximize yield and throughput, it is preferred that DSIDA be charged as a 38% to 44% by weight aqueous solution. DSIDA concentrations less than about 38% may negatively impact throughput while concentrations in excess of about 44% can cause material handling and process problems associated with the resultant slurries which may be thick and viscous. A $PCl_3$ to $Na_2IDA$ molar ratio of 0.8 to 1.4 is preferred, with a ratio of 1.0 to 1.2 further preferred. The reaction is preferably carried out at reflux temperature which is generally between about 100° C. and about 120° C.

In a second step, the hydrolyzate slurry containing the strong acid salt of iminodiacetic acid, sodium chloride, hydrochloric acid and phosphorous acid is transferred from the hydrolyzer to a phosphonomethylation (PM) reactor. In the PM reactor, the slurry is combined with a source of formaldehyde to produce a PM reaction mixture containing PMIDA. Suitable formaldehyde sources include formalin, paraformaldehyde and formaldehyde, with 30-50% formalin being preferred. The formaldehyde and phosphorous acid react with the IDA free base that is in equilibrium with the IDA.HCL, with the product PMIDA being thereby solubilized into the reaction solution as the HCl salt. The formaldehyde source is metered into the phosphonomethylation over an addition time period thereby maintaining IDA in molar excess until the end of the reaction. In this way, the formaldehyde is quickly consumed thereby maintaining it as the limiting reagent. A PMIDA supersaturation critical point of about 20% to about 30% by weight is reached after more than about 60% of the formaldehyde has been charged resulting in nearly instantaneous PMIDA nucleation and crystallization. The remainder of the $CH_2O$ charge is added thereafter with generated PMIDA continuously crystallizing onto the formed crystals as the reaction proceeds.

As formaldehyde is progressively added and PMIDA.HCL accumulates, IDA.HCL is progressively depleted while the solubility of IDA.HCL in the reaction medium is increased. Generally, residual IDA.HCL becomes fully solubilized before PMIDA crystallization occurs.

According to one process alternative, the entire DSIDA charge is added to the hydrolyzer, and the formed IDA.HCL slurry containing NaCl and phosphorous acid is transferred to the PM reactor. Formaldehyde is then metered into the PM reactor to phosphonomethylate the IDA.HCL. A molar excess of phosphorous acid and formaldehyde is preferred to ensure substantially complete conversion of IDA to PMIDA, with a $CH_2O$ to IDA molar ratio of about 1.10 to about 1.25 being especially preferred. A formaldehyde addition time sequence of about 30 to about 90 minutes is preferred with about 60 minutes being more preferred. Preferably the PM reaction is conducted at reflux temperature which is typically in the range of between about 105° C. and about 145° C., at a pressure of between about 0 psig (1.03 kg/cm² absolute) and about 35 psig (3.16 kg/cm² absolute). More preferred operating temperatures and pressures are in the ranges of between about 115° C. and 140° C. and between about 15 psig (2.08 kg/cm² absolute) and about 25 psig (2.7 kg/cm² absolute).

A preferred process alternative, as described in U.S. Pat. No. 4,775,498 (generally described above) and depicted in FIG. 1 herein, allows the consumption of mineral acid (e.g., HCl) that is added independently of $PCl_3$ to be reduced or eliminated. In this preferred option, the DSIDA charge is divided between the hydrolyzer and the phosphonomethylation reactor. Only the portion of the HCl released in the hydrolyzer is consumed therein in formation of the IDA.HCL salt. The remainder of the DSIDA is added to the PM reactor and is converted to the acid salt in situ by HCl released upon consumption of IDA.HCL in the phosphonomethylation reaction and any free HCl remaining in solution. In this manner HCl usage is maximized and optimized. It is preferred to add about 55% to about 80%, and more preferably about 60% to about 75% of the DSIDA to the hydrolysis reaction, with the remaining DSIDA being added to the PM reactor. Preferred operating temperatures and pressures for the phosphonomethylation reaction are in the ranges of between about 115° C. and 140° C. and between about 15 psig (2.08 kg/cm² absolute) and about 25 psig (2.7 kg/cm² absolute). In this embodiment, the PMIDA supersaturation critical point of about 20% to about 30% by weight is reached after more than about 70% of the formaldehyde has been charged resulting in nearly instantaneous PMIDA nucleation and crystallization.

In the PM reaction, it is preferred to meter formaldehyde into the reaction solution thereby maintaining it as the limiting reagent and thus controlling the rate at which PMIDA is generated. Formaldehyde is preferably charged over a time period of between about 20 minutes and about 180 minutes, between about 30 minutes and about 120 minutes, or even between about 45 minutes and about 90 minutes. Controlled addition enables a substantially homogeneous mixture to be maintained thereby preventing high localized $CH_2O$ concentrations resulting in "hot spots" of high PMIDA concentration, premature nucleation and the promotion of undesired side reactions. By controlling the reaction rate, the PMIDA concentration in the reaction solution can be slowly increased up to the point of supersolubility before nucleation and crystallization occur. This is desired because, for example, premature crystallization can entrap unreacted IDA as an impurity as well as give a formed crystal morphology that detrimentally varies considerably from batch to batch.

The overall reaction for the hydrolysis and phosphonomethylation steps is as follows:

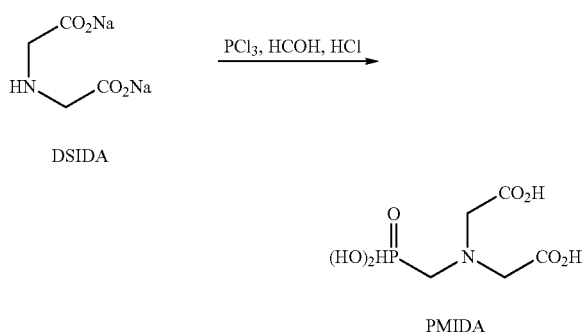

DSIDA

PMIDA

In a third step of the PMIDA process, base is added to adjust the PM reaction mixture containing PMIDA to a pH of about the PMIDA isoelectric pH point. That pH is the point of minimum PMIDA solubility. The adjusted PM reaction mixture is then transferred to a crystallizer (see FIG. 1) where it is then cooled to about 50° C. to about 20° C. over a period of about 0.5 hours to about 10 hours. Water is added to dissolve NaCl and PMIDA crystals are then collected as a wetcake and dewatered using solid/liquid separation equipment known in the art such as filters and centrifuges. The wetcake is washed with water or in a counter-current scheme using weak process liquors and/or water to reduce the level of impurities. The washed wetcake is then reslurried for use in the manufacture of an N-(phosphonomethyl)glycine product (i.e., glyphosate or a salt of glyphosate) by means known in the art. N-(phosphonomethyl)glycine prepared by the liquid phase oxidative cleavage of PMIDA may be converted to a salt of glyphosate such as an alkali metal salt (e.g., sodium or potassium), alkanolamine salt (e.g., isopropylamine), alkyl amine salt (e.g., dimethylamine) or alkylsulfonium salts (e.g., trimethylsulfonium). Glyphosate or its salt is transferred to railcars or seatainers for bulk shipment, or dried by methods known in the art such as spray dryers or fluidized bed driers. About 80% to about 90% of PMIDA crystallization occurs in the phosphonomethylation reactor with the remaining about 10% to about 20% of the PMIDA being removed from solution in the crystallizer.

Although high yields of PMIDA are obtained from the prior art processes, impurities are formed from reaction byproducts and raw material contaminants during both the hydrolysis and PM reaction steps. Those impurities include, for example, NaCl, N-methyl IDA, IDA, N,N-bis(phosphonomethyl)glycine ("glyphosine"), glycine, unreacted formaldehyde, and N-methyl-N-(phosphonomethyl)glycine ("NMG"). Glycine and sarcosine are two problematic raw material contaminants that can be present in DSIDA. Quantitative amounts of glyphosine can be generated in the PM reaction step, by phosphonomethylation of glycine according to the following reaction:

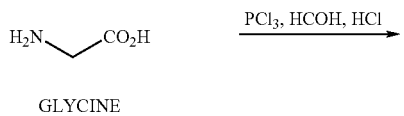

GLYCINE

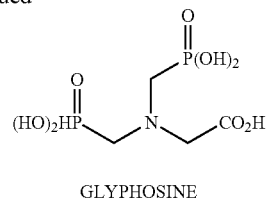

GLYPHOSINE

NMG can be produced in the PM reaction step from glycine or by phosphonomethylation of sarcosine according to the following reaction:

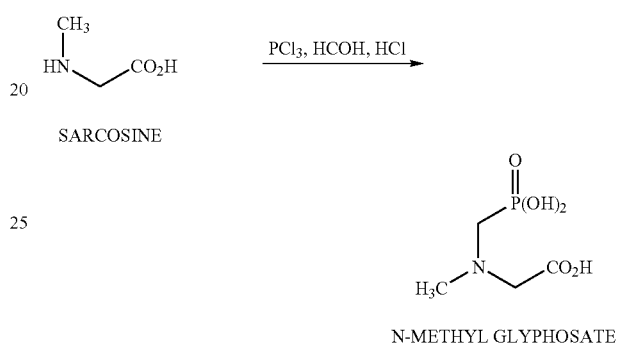

SARCOSINE

N-METHYL GLYPHOSATE

Glyphosine and NMG may also be produced by the degradation of PMIDA in a reaction sequence wherein an acetic group is cleaved from PMIDA to form glyphosate, which can then be converted to either glyphosine via phosphonomethylation or NMG by methylation. Based on experimental evidence to date, it is believed that somewhat limited PMIDA degradation can occur at PM reaction temperatures in excess of about 115 to 120° C. Glyphosine formation from PMIDA can be problematic, however, at temperatures in excess of about 115 to 120° C. where the PMIDA concentration is supersaturated and the time of high temperature exposure exceeds about 30 minutes, 25 minutes, 20 minutes, 15 minutes, 10 minutes or even 5 minutes.

PMIDA Crystallization

PMIDA crystal generation and growth may be generally characterized as a two-step process. In a first step, solid phase crystal nuclei are formed in a supersaturated PMIDA solution in a phase termed "nucleation." In a second step crystal growth occurs by accretion as additional PMIDA moves from the liquid supersaturated phase to the solid crystal phase. The degree of supersaturation decreases, or "relaxes," as crystallization proceeds. Crystallization essentially stops when the PMIDA solution reaches the saturation point.

Nucleation may generally be defined as the process by which new crystals are formed from supersaturated solutions. Crystals typically originate as microscopic nuclei from which the crystals grow. In a crystal-free solution, nucleation must first take place for supersaturation to be relaxed with resultant crystal growth. The formation of microscopic nuclei from supersaturated reaction solutions that do not contain PMIDA crystals may be referred to as primary nucleation, of which there are two types: homogeneous primary nucleation and heterogeneous primary nucleation. Secondary nucleation refers to the generation of PMIDA nuclei from supersaturated reaction solutions that contain PMIDA crystals.

In general, homogeneous nucleation is defined as the formation of a new phase (i.e., solid crystals from a solution) from a supersaturated phase in the absence of foreign seed particles. In contrast, heterogeneous nucleation results from the presence of some foreign insoluble material. Impurities such as dust, inerts such as filter aids, residual catalyst, and foreign bodies such as bacteria and the like can serve as nucleation sites (i.e., heteronuclei) for crystal growth. Moreover, surface imperfections in process equipment (e.g., vessel walls and impeller surfaces) can serve as heterogenous nucleation sites.

Figure 2:
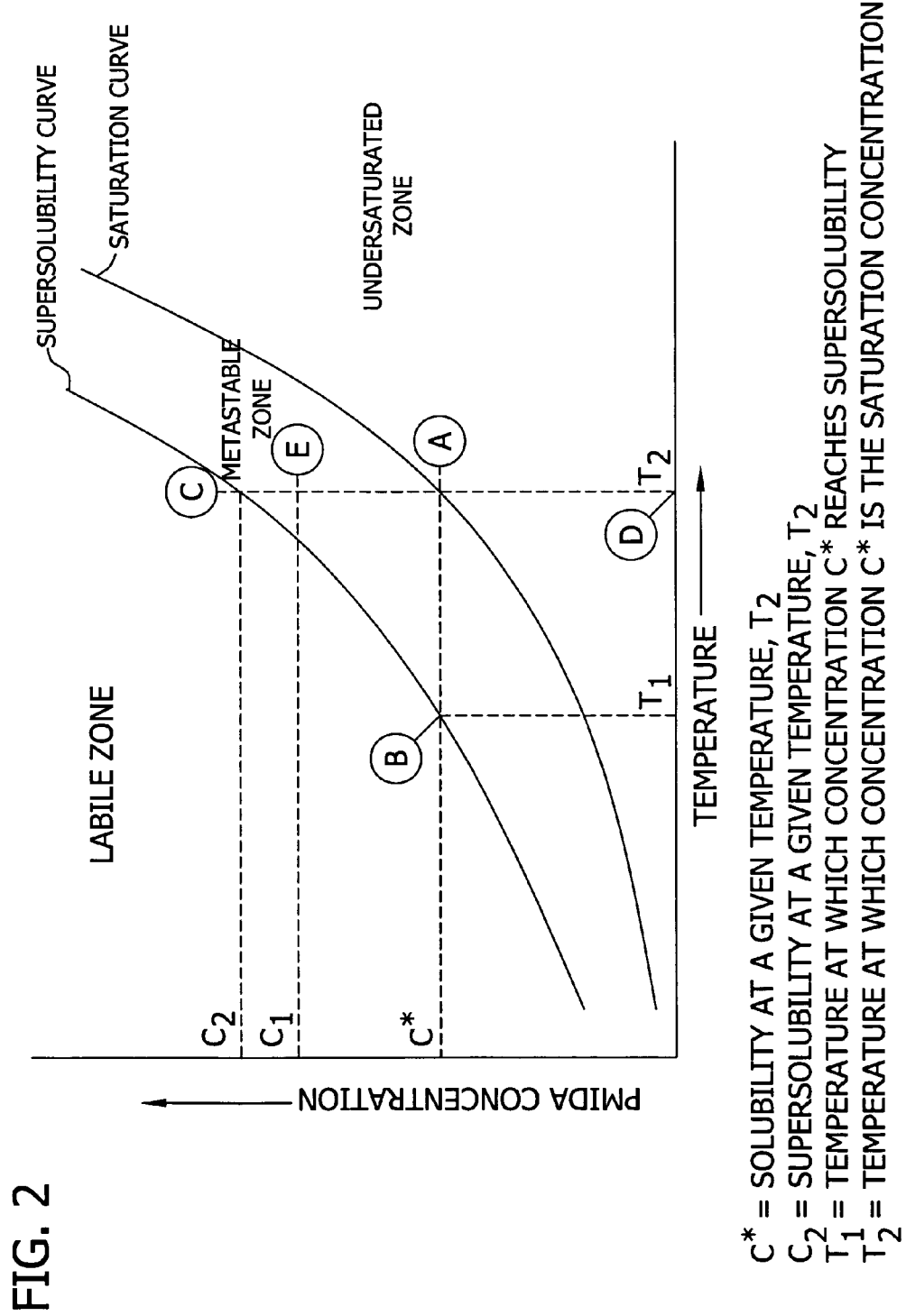
FIG. 2 is a graph representing the relationship between PMIDA saturation concentration and supersolubility saturation concentration versus temperature. It can be understood from the graph that the saturation curve and supersolubility curve form three zones: an undersaturated zone wherein the PMIDA concentration is unsaturated; a metastable zone wherein the PMIDA concentration is supersaturated; and a labile zone wherein the PMIDA concentration exceeds the supersaturation concentration.

Homogeneous nucleation of solid particles from a liquid has been studied theoretically and published references are readily available. See, for example, J. W. Mullin, "Crystallization" $3^{rd}$ edition (1992), Butterworth-Heinemann. Under one theory, and without being bound thereto, the initiation of homogeneous nucleation depends on the formation of small atom clusters that arise during collisions. In reference to FIG. 2, in the undersaturated and metastable concentration zones, the cluster dissolution rate equals or exceeds the cluster formation and growth rate. Hence, a critical cluster concentration is usually not reached. At sufficiently high concentrations, represented by the labile zone, the cluster formation rate drastically increases and clusters with a size larger than a certain size, called the critical size, grow into a new phase. In the case of PMIDA, this process occurs very rapidly in a nucleation burst causing the particles to crash from solution in a crystallization event. That process is represented in FIG. 2 as follows. As the PMIDA reaction proceeds at temperature $T_2$, the PMIDA concentration in solution is first below the saturation point, as represented by the undersaturated zone (the concentration at temperature $T_2$ is less than $c^*$ at $T_2$), where nucleation is improbable. As the reaction further proceeds the PMIDA concentration becomes supersaturated, as represented by the metastable zone (the concentration is between $c^*$ and $c_2$ at temperature $T_2$), wherein nucleation is not likely. Finally, continued PMIDA generation results in the PMIDA concentration passing the point of supersolubility, as represented by the labile zone at point C (concentration $c_2$ at temperature $T_2$) where nucleation is probable. Spontaneous nucleation and crystallization relaxes the PMIDA solution concentration to a point just above point A (concentration $c^*$ at $T_2$) where it remains for the remainder of the reaction. Because a large number of nuclei are spontaneously created and the PMIDA reaction sequence is at least about 50% completed at the point of spontaneous nucleation, it is believed that subsequent crystal growth is limited and the deposition of PMIDA generated subsequently is distributed over a large number of crystals thereby creating a large proportion of fines.

PMIDA crystallization is unique since even though NaCl crystals are present while the solution is supersaturated, nucleation does not occur until the supersaturation level reaches a critical point. It is believed without being bound to any particular theory that PMIDA nucleation can be defined by Equation 1.1:

$$B°=k_1 M_T^j A^I \Delta c^b \quad (1.1)$$

where $B°$ is the number of nuclei per unit volume per time, $k_1$ is dependent upon temperature and the nature of the material, $M_T$ is the slurry specific gravity, A is a measure of the degree of agitation, $\Delta c$ is the amount of supersaturation, and j, I and b are all power function coefficients. Nucleation at low supersaturation levels is generally slow under most circumstances so it can be considered somewhat insignificant. As supersaturation increases, the nucleation rate increases becoming more significant at the boundary between the metastable zone and labile zone. The boundary between the zones may be difficult to characterize and depends on variables such as measurement accuracy of the rate of supersaturation generation, temperature, temperature flux, PMIDA concentration, impurity concentration, and the like. In the labile zone, nucleation is generally probable. During nucleation, the initial crystal surface area is small so that the supersaturation level may remain in the labile zone for a significant period.

Crystal growth occurs once sufficient nuclei are present. PMIDA crystal growth rate may be characterized kinetically as being a function of a concentration driving force: the concentration present in solution versus the concentration that would be present at the same temperature at saturation equilibrium. That equilibrium concentration is generally the maximum solubility at that temperature. The concentration driving force may also be termed as the degree of supersaturation, with supersaturation level being a measure of the concentration force for crystallization. Supersaturation is often expressed as the concentration difference, $\Delta c = c - c^*$, where $c^*$ is the equilibrium saturation at a given temperature, and c is the solution concentration. $c^*$ is a function of both temperature and the extent of reaction. In reference to FIG. 2, if the solution concentration is $c_1$ (point E), and the equilibrium saturation is $c^*$ (point A), the degree of supersaturation ($\Delta c$) would be the difference between $c_1$ and $c^*$. The higher the level of supersaturation, the greater the driving force for crystallization.

The degree of supersaturation, or concentration driving force, may be expressed in a number of ways. One particularly useful expression, sigma ($\sigma$), is an isothermal measure of absolute, or relative, supersaturation. Sigma may be defined as the difference between the solution concentration and saturation concentration divided by the saturation concentration at a specified temperature. In reference to FIG. 2, $sigma_{max}$ may be defined as the difference between the critical supersaturation concentration and the saturation concentration divided by the saturation concentration at that temperature, or $\sigma_{max}=(c_2-c^*)/c^*$. It follows that $sigma_{min}$ is equal to 0 as at the point that the solution concentration and saturation concentration are the same ($\sigma_{min}=(c^*-c^*)/c^*$).

It is believed, without being bound to any particular theory, that crystal growth may take place according to Equation 1.2:

$$i. \ G=dl/dt=k_2(\Delta c)^g \quad (1.2)$$

where G is the growth rate of unit length per unit time, $k_2$ is dependent upon temperature and material, $\Delta c$ is the amount of supersaturation, and g is a material-dependent constant which is usually between about 1 and about 2. The term $k_2$ varies with temperature according to the Arrhenius equation $k_2=A^*\exp(-E_G/RT)$, where A is a constant and $E_G$ is the activation energy. $k_2$ has been found to vary, among other variables, with surface area, impurities and temperature. For example, $k_2$ values of 1.5 $hr^{-1}$ and 0.6 $hr^{-1}$ have been estimated for PMIDA crystallization at about 50° C. in essentially pure PMIDA liquor and PMIDA in process mother liquor, respectively. Moreover, $k_2$ at 30° C. in process mother liquor has been estimated at 0.34 $hr^{-1}$. Therefore, seeding at high $\Delta c$ values and at high temperature ($T_h$) results in a rapid initial growth rate followed by concentration decrease to a lower $\Delta c$ value thereby providing a slower secondary growth rate.

Crystal growth may be described mechanistically. In one theory for the mechanism of small crystal formation termed the diffusion theory, and without being bound to any particular theory, it is believed that a large number of fines are generated in the prior art processes because the rapid nucleation results in a large number of nuclei and the concentration of PMIDA remaining in solution after rapid initial crystallization exhibits a low degree of supersaturation thereby enabling little additional crystal growth. In the diffusion theory, rapid nucleation can cause the crystal formation kinetics (rate) to exceed diffusion kinetics. Under this theory a crystal is surrounded by a boundary layer located between the crystal and the mother liquor. When crystal formation kinetics do not exceed diffusion kinetics, crystallization rate is controlled by the rate at which the material can diffuse through the boundary layer to the surface of the crystal. In such a case the nucleation rate and crystal growth rate (1) are in substantial equilibrium or (2) growth predominates over nucleation, thereby limiting the number of nuclei, hence the proportion of fines. The number of finished crystals is fixed and limited by the number of nuclei thereby resulting in crystals of relatively large size. When the formation kinetics exceed the diffusion kinetics, as in the case of spontaneous nucleation, crystal growth can move from diffusion control to surface reaction control, but the basic nucleation mechanism remains unchanged. The result is nucleation predominates over growth, hence the rate of nucleation continues to increase while the growth rate levels off. Those effects may cause the relative number of nuclei to increase resulting in a large number of finished crystals of reduced average size, a consequence manifested in a large proportion of fines.

The small particles may cause formed PMIDA wetcake beds characterized by low porosity and impermeability resulting in solid-liquid separation inefficiency. It has been determined that crystal bed porosity can be affected by a combination of morphological factors including crystal size and crystal size distribution, crystal thickness and effective surface area. Crystal bed porosity impacts the PMIDA purification process efficiency in several ways. For example, low porosity causes inefficient dewatering with excess impurity-laden mother liquor left in the crystal bed; extended dewatering times and/or wet crystals result. Moreover, crystal-washing efficiency is decreased as wash water penetration of the crystal bed is inhibited thereby reducing the amount of chlorides and other impurities that may be extracted from the bed. The result is excess wash water may be required to achieved desired crystal purity.

Exacerbating the crystal morphology-based PMIDA processing issues is an elevated impurity content. Under a general model, it is believed that at the core of a PMIDA crystal a certain level of impurities are present due to the co-crystallization of PMIDA and impurities such as, for example, glyphosine and chlorides. Experimental evidence indicates that after repeated washing of the crystals, the impurity level of the crystals approaches a steady-state level which reflects the impurity content of the core. As the crystal grows, an impurity gradient is formed because the impurities are unable to diffuse out of the forming crystal at an effective rate. The diffusion rate is impurity-dependent, thus each impurity may have a unique gradient. Because the prior art PMIDA crystals are formed by crashing from solution at an elevated level of supersaturation, the crystals are formed very rapidly. Based on experimental evidence to date, it has been discovered that rapid PMIDA crystallization can cause the crystals formed to include a higher impurity content than would a comparable slower, controlled crystallization. Impurities that may be included in the formed crystal include, as described above, for example, NaCl, N-methyl IDA, IDA, N,N-bis(phosphonomethyl)glycine ("glyphosine"), glycine, unreacted formaldehyde, and N-methyl-N-(phosphonomethyl)glycine ("NMG"). In the case of glyphosine, based on experimental evidence, the ratio of wetcake glyphosine concentration to mother liquor glyphosine concentration was calculated for non-seeded PM reactions and PM reactions seeded at low $\sigma$ (early seeding), intermediate $\sigma$ (intermediate seeding) and high $\sigma$ (late seeding) and was found to be 1.88:1, 1.45:1, 1.59:1 and 1.64:1, respectively. Therefore, seeding reduces the amount of glyphosine partitioning to the wetcake.

Nucleation and growth rates are important not only in formed PMIDA crystal morphology, but also in incorporation of impurities in the prepared solid PMIDA. It is believed without being bound to any particular theory that the effective impurity-partitioning coefficient, $K_{eff}$, may be defined by Equation 1.3:

$$K_{eff}=K^*\exp(\delta G/D) \qquad (1.3)$$

where G is the crystal growth rate, D is the molecular diffusivity of impurity in solution, and $\delta$ is a parameter related to the diffusion boundary layer thickness. K* is the equilibrium-partitioning coefficient, which is the impurity concentration in solid divided by the impurity concentration in solute. In general terms, impurity incorporation increases with higher crystal growth rates because of the fact that crystalline structures require a certain amount of time to settle into their equilibrium positions to avoid causing defects in the structure. These defects, which can be referred to as voids, can provide sites for impurity inclusion. Because of the voids, the effective impurity coefficient, $K_{eff}$, is higher than the equilibrium-partitioning coefficient. From a concentration standpoint, the major impurity present in PMIDA is chlorides in the form of NaCl. Rapid, uncontrolled crystal growth may increase the contained chloride content in PMIDA crystals by, for example, the primary or secondary impurity inclusion mechanisms described below. Mother liquor chloride content is typically about 14% to about 15% by weight while the chloride content in unwashed PMIDA wetcake is generally about 1% to about 4% by weight. Chloride content in finished PMIDA is preferably less than or equal to about 1000 ppm (i.e., about 0.1%). Hence, the PMIDA crystals must be purified with an efficiency of greater than about 90% to meet finished product purity requirements.

Figure 3:
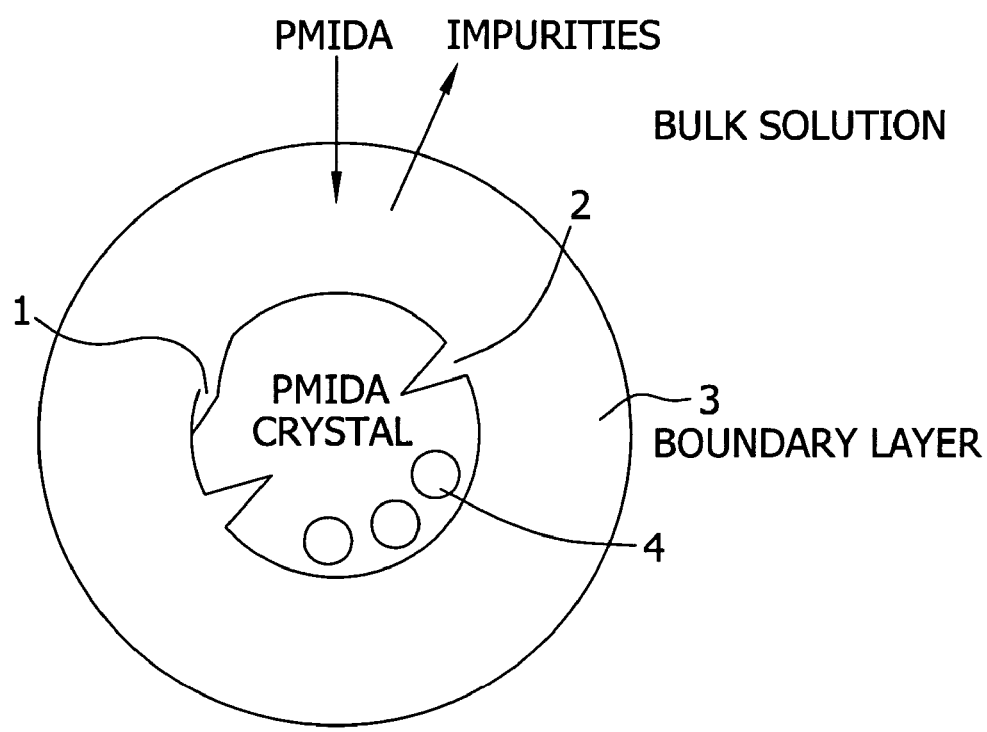
FIG. 3 depicts the primary and secondary PMIDA crystal impurity incorporation or inclusion mechanisms.

In one theory for the mechanism of impurity inclusion, and without being bound to any particular theory, in a mechanism termed primary inclusion as depicted in FIG. 3, a growing PMIDA crystal is surrounded by a boundary layer (3) in immediate contact with both the outer crystal surface and the PMIDA bulk solution. Growth on the PMIDA crystal is a two-step process whereby in a first step a solute molecule must diffuse from the bulk of solution, through the boundary layer and to the crystal surface. In a second step, once the solute molecule reaches the crystal surface it must orient itself into the crystal lattice. The boundary layer is a dynamic zone wherein as crystallization proceeds, PMIDA diffuses from the boundary layer and crystallizes onto the crystal surface resulting in an elevated impurity to PMIDA ratio in the boundary layer as compared to the surrounding bulk of solution. Replenishment of the boundary layer with PMIDA depends on diffusion from the bulk solution into the boundary layer. Even if diffusion of PMIDA is equivalent to the rate of crystallization, the ratio of impurities/PMIDA progressively increases until the impurity content of the boundary layer is equal to that of the bulk solution. Even at a constant impurity concentration in the boundary layer, if the crystal formation kinetics (rate) is faster than the rate of impurity diffusion then the ratio of impurities to PMIDA in the boundary layer may continue to increase as compared to the bulk of solution and the forming crystal therefore can trap, or include, progressively more elevated levels of impurities in the solidified PMIDA resulting in a relatively impure crystal, especially in its outer margin. Experimentation appears to support the impurity diffusion mechanism as it has been determined that levels of impurities in the crystal wetcake are typically much higher than the bulk mother liquor indicating that impurity inclusion is more than merely retention of mother liquor, and that relative rates of PMIDA and impurity diffusion are affected by crystallization rate.

Fast crystal growth can also trap impurities in a mechanism termed secondary inclusion. Fast crystal growth may lead to non-uniform growth rates and resulting formed layer thicknesses that impart mechanical instability. As depicted by FIG. 3 at point 2, an irregular, cracked crystal may form with cavities that increase inclusion potential by enabling liquor to pool in the crystal. Further, non-uniform growth can result in several crystal layers forming simultaneously. In that case, a gap (FIG. 3 at point 1) can form at the layer interface that may then be covered by an overlapping layer thereby trapping a pocket of liquor (FIG. 3 at point 4).

Experimentation seems to support the primary and secondary inclusion theories of PMIDA impurity contamination. Repeated washing of PMIDA wetcake having a relatively high impurity concentration reduced the impurity concentration by only about one third. This suggests that while a some amount of impurities is located at or near the crystal surface, the majority of the impurities are trapped within the crystal lattice, and dissolution of the PMIDA is necessary to remove them.

Based on experimental evidence to date, it is believed that the extent of impurity partitioning to the PMIDA wetcake is reduced when the crystallization is relatively slow and the agitation is efficient. Baseline, or comparative, experiments performed in non-seeded systems at a cooling rate of about 1° C. per minute indicate that the partitioning of glyphosine and NMG to the wetcake is about 34% and about 25%, respectively. In a controlled cooling experiment whereby cooling was done at a rate of about 0.1° C. to 1° C. per minute, the partitioning of glyphosine and NMG to the wetcake was reduced to about 11% and about 6%, respectively, as compared to baseline experiments performed in non-seeded systems at a cooling rate of about 1° C. per minute. Thus, impurity partitioning to the PMIDA wetcake can be reduced by controlling the cooling rate of the PM reaction mixture. Moreover, it is believed that impurity incorporation and the PM reaction mixture agitation rate are inversely related. Under one theory, and without being bound to any particular theory, increased agitation speed can result in decreases in boundary layer thickness and more efficient PMIDA and impurity diffusion. For example, in two sets of experiments, all the variables between the experiment set were kept constant except the agitation rate. An increase in agitation rate from 250 rpm to 500 rpm resulted in a reduction in the concentration of glyphosine and NMG in the wetcake, with about a 40% reduction in glyphosine partitioning to the wetcake (weight percent basis) and a wetcake NMG concentration decrease of about 20% (weight percent basis).

Based on experimental evidence to date, it is also believed that the impurities in PMIDA wetcake do not predominantly occur because of solubility restraints. It has been determined that glyphosine and NMG are more soluble in PMIDA mother liquor than is PMIDA. For example, the glyphosine and NMG solubility limits at room temperature (about 25° C.) in PMIDA mother liquor having a relatively high impurity content were found to be about 3.9 wt % and about 3.6 wt %, respectively. Those solubility limits are higher than the impurity concentration typically encountered in the prior art processes, thus it is believed that it is unlikely that impurity partitioning to the PMIDA wetcake results from solubility considerations such as impurities precipitating from solution onto the forming PMIDA crystal.

Experimental data indicate that the mechanism behind NMG incorporation in PMIDA wetcake is more a function of crystallization rate rather than the concentration of NMG in the mother liquor. In one set of experiments for instance, prior to the PM reaction, the PM reactor was spiked with NMG at rates of about 0.10 wt % and 0.55 wt % on a final batch weight basis. Resulting levels of NMG in the PMIDA wetcake were found to be about 1100 ppm and about 5200 ppm, respectively. While the NMG concentration in the wetcake decreased as NMG spikes were decreased, the associated NMG partitioning percentage stayed relatively constant at about 25%. Hence NMG partitioning to the PMIDA wetcake appears to be essentially independent of concentration. Similarly, glyphosine spiking experiments indicate that the partitioning percentage remains fairly consistent regardless of the glyphosine mother liquor concentration.

Experimental data further indicate that PMIDA solubility exhibits exponential temperature dependence. For instance, mother liquor recovered at the end of a commercial scale batch was acidified with HCl in order to have an HCl content approximately equivalent to that found at the end of the PM reaction. PMIDA solubility in that mother liquor was measured and is reported in Table A below as "PM (wt %)".

TABLE A

PMIDA Solubility in PM Mother Liquor

| Temp (° C.) | PM (wt %) |
|---|---|
| 115 | 8.72 |
| 90 | 4.15 |
| 70 | 2.29 |
| 50 | 1.26 |
| 20 | 0.52 |

PMIDA solubility limits change throughout the PM reaction making supersaturation prediction problematic. Several laboratory experiments were performed at 105° C. using a 60:40 DSIDA split between the hydrolyzer and PM reactor in order to evaluate supersaturation limits during seeding and the initial stages of the crystallization event. The PM feed amounts were altered such that only a portion of the typical feed amounts were used in order to simulate various stages of the PM reaction step. Experimental data indicate that as the reaction proceeds, PMIDA solubility decreases. It is believed, without being bound to any particular theory, that as NaCl is produced during the PM reaction, and HCl is consumed, PMIDA solubility is suppressed. Table B presents PMIDA solubility in the PM reactor mother liquor at varying amounts of formalin addition.

TABLE B

PMIDA Solubility in PM Mother Liquor throughout PM reaction

| % of total formalin added to PM reactor | Equilibrium PMIDA in PM mother liquor (wt %) |
|---|---|
| 40% | 12.6% |
| 70% | 8.6% |
| 100% | 5.9% |

Figure 4:
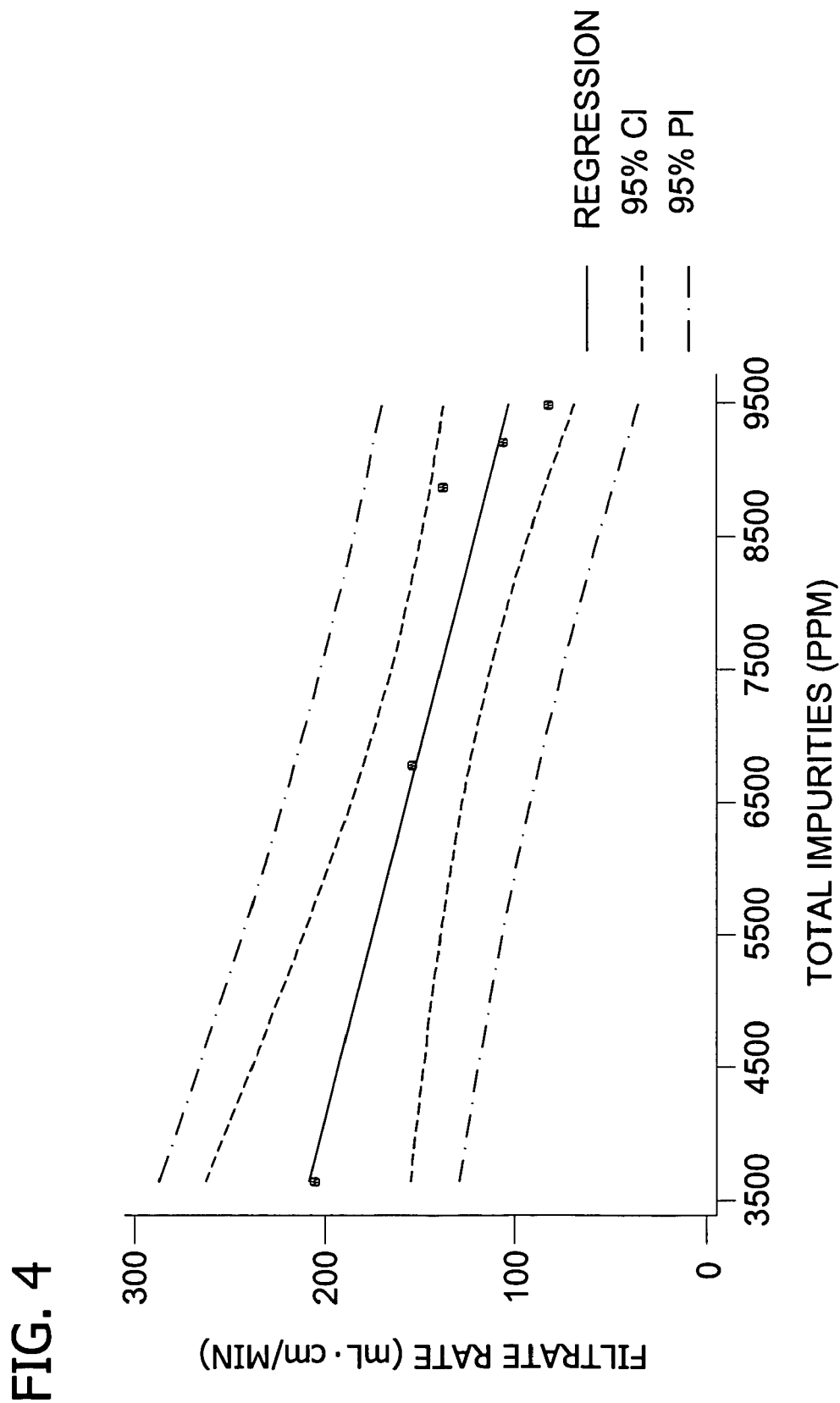
FIG. 4 is a graph representing the relationship between PMIDA crystal impurity concentration and crystal wetcake filtration rate.
Figure 5:
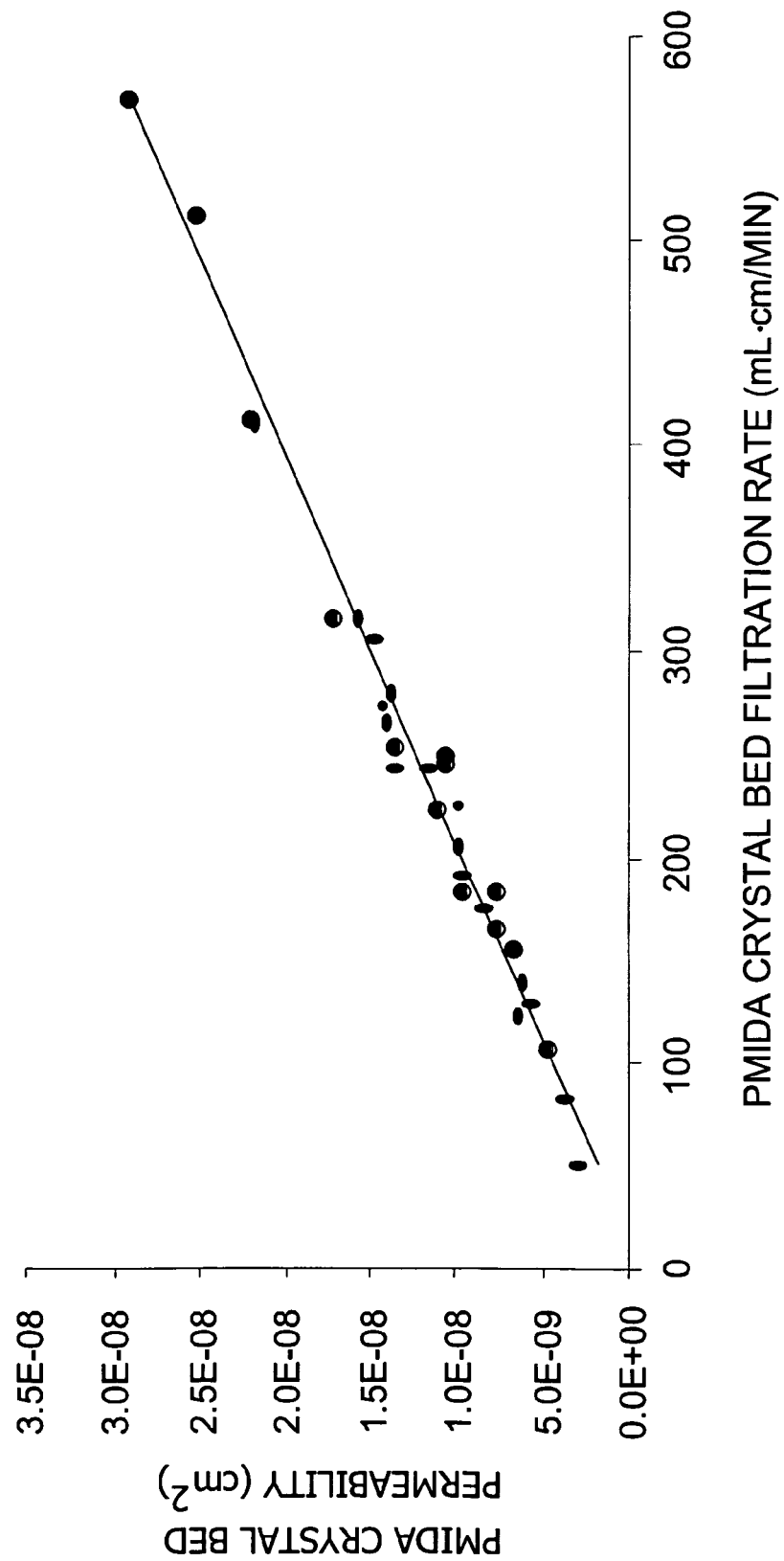
FIG. 5 is a graph representing the relationship between PMIDA crystal permeability and crystal wetcake filtration rate.

Aside from the problem of inclusion of impurities into the crystal structure, impurities have also been found to affect the PMIDA slurry filtration performance. For instance, as depicted in FIG. 4, and as demonstrated in Example 10, in seeded crystallization systems it was shown that PMIDA wetcake filtration performance (as indicated by the modified filtration rate in mL·cm/min) decreases linearly as the slurry impurity concentration increases. The modified filtration rate is a measure of wetcake permeability and is calculated by multiplying the liquid filtration rate (mL/min) by the wetcake thickness. Seeded crystallization systems can yield crystallized PMIDA beds having a modified filtration rate of at least about 5 mL cm/min. In particular, it has also been discovered, as depicted in FIG. 5, that filtration performance (mL·cm/min) generally increases linearly as the cake permeability ($cm^2$) increases, with a doubling of permeability providing approximately a two-fold increase in filtration rate.

The prior art crystallization sequence may be characterized as consisting of four phases as follows. In reference to FIG. 2, and assuming the PMIDA reaction is conducted at reflux temperature $T_2$, in a first phase, the PMIDA concentration increases as the formaldehyde is added, but remains below the point of saturation in the reaction system. The first phase is represented by the undersaturated zone depicted in FIG. 2, and in particular by the isothermal line segment from point D (initial PM IDA concentration) to point A (the PMIDA saturation concentration at $T_2$, or $c^*$). In the undersaturated, or stable, zone crystallization is improbable because there is no supersaturation, hence insufficient driving force for crystallization.

In a second crystallization phase, as the reaction continues the PMIDA concentration enters the metastable zone as depicted in FIG. 2 by the isothermal line segment from point A (the saturation concentration, or $c^*$) to point C (the critical supersolubility limit, or $c_2$). In the metastable zone, between the points of maximum solubility and maximum supersolubility, the solution is supersaturated but the level of supersaturation is generally not high enough to drive nucleation and crystallization, i.e., spontaneous crystallization.

In a third crystallization phase, the reaction continues with the PMIDA concentration increasing along the $T_2$ isothermal past point C (i.e., the concentration exceeds $c_2$) into the labile zone. Concentrations within the labile zone exceed the limit of supersolubility and are unstable, with the level of supersaturation being sufficient to drive spontaneous nucleation. Spontaneous, uncontrolled, nucleation and crystallization of PMIDA occurs with the result being PMIDA crashing from solution. The PMIDA concentration then "relaxes" to $c^*$ or slightly greater.

In a last crystallization phase a dynamic system of continuous PMIDA generation and crystallization occurs as formaldehyde addition continues. In this phase the PMIDA concentration remains at or slightly above $C_1$ with continual crystallization of PMIDA onto the formed nuclei occurring until the reaction is complete.

The crystals generated by processes known in the art have been found to have a number average particle size of about 7.5 μm with a large amount of fines. In those processes excessive nucleation occurs at a very high degree of supersaturation, is catastrophic, and may result in too many nuclei being formed at high supersaturation thereby yielding poor crystals with a high proportion of fines. Once excessive nucleation occurs, the material balance allows only limited growth of particles resulting in a particle size distribution skewed toward smaller, or fine, particles which thereafter produce densely packed crystal beds of generally low porosity giving filter and centrifuge cakes that are resistant to dewatering and washing. The solid-liquid separation inefficiencies cause inefficient equipment utilization and result in throughput penalties of as much as about 10% to 20%.

Although the prior art processes provide a useful commercial process for the preparation of PMIDA, the crystallization procedure presents certain purity and processing issues, heretofore unsolved, that the present invention overcomes thereby providing significant advancements in both efficient commercial preparation and environmental burden reduction.

PMIDA Seeding

It has been discovered that PMIDA crystal purity and morphology may be reliably controlled to meet predetermined criteria by selectively seeding PMIDA reaction solutions at discrete stages of the phosphonomethylation reaction, or continually over one or more periods during the reaction. Preferably, the process comprises seeding supersaturated PMIDA solutions at discrete degrees of supersaturation thereby fixing both the number of PMIDA crystals and the rate at which they grow. Moreover, that control may be achieved in dynamic process systems where formaldehyde feed, PMIDA generation and crystallization are concurrent. Seeding is effective in embodiments where the entire DSIDA charge is fed to the PM reactor, as well as embodiments where the DSIDA charge is split between the hydrolyzer and PM reactor, such as a hydrolyzer to PM reactor charge ratio of 60:40 or 75:25. Seeding at a concentration less than the critical supersaturation concentration enables selective control of PMIDA crystal nucleation and growth rates thereby allowing optimization of crystal size distribution and formed crystal purity.

Important to the inventive method of controlling PMIDA crystal morphology and purity through seeding is the discovery that PMIDA possesses a wide metastable zone. For example, in reference to FIG. 2, a solution of fixed concentration at point A (i.e., concentration $c^*$ at temperature $T_2$) can be cooled to temperature $T_1$ at which point, B, the supersolubility maximum is reached. The solution passes into the labile zone with further cooling. It has been discovered that a saturated PMIDA solution may be cooled by about 35° C. to about 40° C. before crystallization occurs. As another measure, metastable zone width is defined as the concentration difference between the supersolubility and solubility concentrations at an isothermal temperature. In reference to FIG. 2, the metastable zone concentration width at temperature $T_2$ may be defined as the difference between the concentration at point C (i.e., $c_2$) and the concentration at point A (i.e., $c^*$). In the case of the PMIDA reaction, both the saturation concentration and the supersaturation concentration vary during the course of the PM reaction, thus the width of the isothermal metastable zone varies during the reaction. It has been found that the PMIDA isothermal metastable zone is relatively wide and can be as high as about 20 wt % on a PMIDA basis. A wide metastable zone allows selective seeding at discrete points thereby enabling crystals to be designed to meet predetermined standards of morphology and quality.

Through expression of PMIDA supersaturation isothermal concentration on a relative basis in terms of σ, PMIDA has been found to exhibit a broad σ range of 0 to about 2 at the phosphonomethylation reaction reflux temperature. Hence, in the prior art PMIDA processes, spontaneous nucleation occurs at a σ value in excess of about 2, a point where a high degree of concentration driving force is present. Determination of σ may be done by any means known in the art. For example, σ can be estimated based on the total amount of formaldehyde charged to the PM reactor. Based on mass balance calculations known to those skilled in the art, and under process conditions of the prior art processes, it can be estimated that a saturated solution (i.e., σ equal to about 0) is reached at the time at which about 30% to about 35% of the formaldehyde charge has been added. Experiments have shown that the point of critical supersaturation (i.e., σ equal to about 2) occurs after about 65% to about 75% has been charged. Alternatively, σ may be calculated through measured values for the PMIDA concentration and the equilibrium concentration. The relationship between cumulative formaldehyde addition and PMIDA concentration is somewhat linear, hence σ can be estimated based on the amount of formaldehyde charged to the reaction.

Seeding can be used to reduce the peak supersaturation and hence influence particle size distribution, crystal characteristics and related properties. The opportunity for seed addition is largely determined by the width of the metastable zone. Seed crystals should be added close enough to the solubility curve to limit peak saturation. On the other hand, seeding preferably is not initiated until supersaturation levels are high enough for mass crystallization to occur at a sufficient rate. It has been observed that while seeding does increase crystallization rates for low levels of supersaturation, sufficient supersaturation is needed for crystallization to occur at preferred rates. Thus it is generally preferred to add the seed crystals after the solution becomes supersaturated. The seed crystals essentially eliminate, or replace, primary nucleation and provide surface area and allow crystal growth and secondary nucleation to occur without catastrophic nucleation in the labile zone.

As described above, solid/liquid separation equipment known in the art such as filters and centrifuges can be used to collect and dewater PMIDA crystals to produce a bed of PMIDA wetcake. The wetcake bed can then be washed with process liquors and/or water to reduce the level of impurities. The unwashed and/or washed wetcake can characterized in a variety of ways. Physical properties such as filtration rate (mL/min), modified filtration rate (mL·cm/min), cake porosity, cake saturation and cake permeability may be measured and/or calculated as describe herein. Concentrations of Impurities including, for example, NaCl, N-methyl IDA, IDA, N,N-bis(phosphonomethyl)glycine ("glyphosine"), glycine, unreacted formaldehyde, and N-methyl-N-(phosphonomethyl)glycine ("NMG") can be measured by means well known in the art including, for instance, liquid chromatography ("LC"), high pressure liquid chromatography ("HPLC"), ion chromatography, and wet chemistry methods such as, for instance, titration, colorimetry, electrical conductivity, chloride ion-selective electrodes, and loss on drying.

It has been discovered that seeding according to the present invention generates PMIDA crystals and beds comprising crystallized PMIDA having improved physical and purity characteristics as compared to PMIDA crystals and beds of crystallized PMIDA prepared by an otherwise identical process in which no seed crystals are introduced. For example, PMIDA crystal median chord length may be increased by about 2%, 4%, 6%, 8% and even 10%. PMIDA crystal bed permeability may be increased by about 10%, 15%, 20%, 25%, 50% and even 75% over non-seeded material. In particular, PMIDA crystal beds having a permeability of at least about $1 \times 10^{-9}$ cm$^2$, $2 \times 10^{-9}$ cm$^2$, $3 \times 10^{-9}$ cm$^2$, $4 \times 10^{-9}$ cm$^2$, $5 \times 10^{-9}$ cm$^2$, $6 \times 10^{-9}$ cm$^2$, $7 \times 10^{-9}$ cm$^2$, $8 \times 10^{-9}$ cm$^2$, $9 \times 10^{-9}$ cm$^2$ or even about $1 \times 10^{-8}$ cm$^2$ can be prepared. PMIDA crystal bed porosity can be increased by about 2%, 4%, 6%, 8% and even 10%. In one measure, an equilibrium partitioning coefficient is calculated by dividing the impurity concentration in the solid (i.e., crystals) by the impurity concentration in the solute (i.e., mother liquor). Seeding improves PMIDA crystal and formed crystal bed purity is improved by reducing total impurity partitioning to PMIDA crystals, as indicated by impurity partitioning coefficient reductions, of about 5%, 10%, 15% and even 20%. NMG crystal bed concentration reductions, on a part per million (ppm) basis, of about 2%, 4%, 6%, 8%, 10%, 15% and even 20% can be attained. In particular, PMIDA having an NMG content of less than about 10,000 ppm, 9,000 ppm, 8,000 ppm, 7,000 ppm, 6,000 ppm, or even 5,000 ppm on a dry weight basis can be prepared. Glyphosine crystal bed concentration reductions, on a weight percent basis, of about 2%, 4%, 6%, 8%, 10%, 15% and even 20% can be attained. In particular, PMIDA having a glyphosine content of less than about 11,000 ppm, 10,000 ppm, 9,000 ppm, 8,000 ppm, 7,000 ppm, 6,000 ppm, or even 5,000 ppm on a dry weight basis can be prepared. PMIDA crystal bed chloride concentration reductions, on a weight percent basis, of about 20%, 30%, 40%, 50%, 60% and even 70% can be attained. In particular, PMIDA having a chloride content of less than about 7,000 ppm, 6,000 ppm, 5,000 ppm, 4,000 ppm, 3,000 ppm, 2000 ppm, 1,000 ppm, 500 ppm or even 250 ppm on a dry weight basis can be prepared.

It has been surprisingly discovered that PMIDA seed crystals may be added to the PM reactor during discrete points in time during the PMIDA reaction sequence in order to selectively optimize particle morphology, size distribution and purity. It is preferred to add seed crystals to the PM reactor while the PMIDA concentration is in the metastable zone. By seeding prior to spontaneous nucleation, the nucleation phase is essentially eliminated and the initial number of crystals is fixed. By selectively seeding at a discrete σ value, initial crystallization driving force, thus crystallization growth, may be controlled. It has been further discovered that by eliminating the dependence on primary nucleation and controlling crystal growth rate via the degree of initial post-seeding supersaturation, batch-to-batch variability of crystal particle size is reduced, particle size distribution is tightened, and purity is increased.

For permeability optimization, it has been discovered that at least about 0.5% by weight seed crystals based on dry PMIDA weight are preferably charged to the PM reactor, more preferably at least about 1 wt %. In particular, it is preferred to charge between about 0.5 wt % and about 6 wt %, between about 1 wt % and about 5 wt %, between about 1 wt % and about 4 wt %, between about 1 wt % and about 3 wt %, and even more preferably between about 1 wt % and about 2 wt %. It is believed, without being bound to any particular theory, that seeding prior to primary nucleation fixes the number of nucleation sites, hence the number of formed crystals. However, the crystallization driving force present at high supersaturation may be such that seeding at about 0.5% provides an inadequate number of nucleation sites thus enabling some nucleation to occur resulting in a certain percentage of generated PMIDA fines. The result may be a permeability improvement over unseeded PMIDA, but such improvement may not be the maximum attainable. Seeding at greater than about 4% may present an excess of nuclei over that preferred for optimum crystal growth, but nonetheless provides a marked permeability improvement over unseeded PMIDA. The result is optimization of the number of crystals at the preferred size and a relative absence of fines.

Seeding also can reduce the amount of glyphosine formed in the PM reaction from the degradation of PMIDA in a reaction sequence wherein an acetic group is cleaved from PMIDA to form glyphosate, which is then phosphonomethylated to form glyphosine. It has been discovered that extended exposure of highly supersaturated PMIDA solutions to temperatures greater than about 115° C. to about 120° C. can favor PMIDA degradation with resulting formation of glyphosine. Seeding reduces the PMIDA concentration from highly supersaturated to slightly supersaturated thereby limiting the time-temperature exposure of highly supersaturated PMIDA solutions and reducing the amount of formed glyphosine. Seeding preferably limits the exposure time of highly supersaturated PMIDA solutions to elevated temperatures to less than about 30 minutes, 25 minutes, 20 minutes, 15 minutes, 10 minutes or even 5 minutes.

Seeding has also been found to be effective in offsetting throughput penalties associated with operation at high pressures, for example 15 psig (2.1 kg/cm² absolute), 20 psig (2.4 kg/cm² absolute), or even 25 psig (2.7 kg/cm² absolute). In commercial operations, it has been observed that wetcake centrifuge capacity decreases and wetcake chloride content increases with increasing PM reaction pressure. It is believed, without being bound to any particular theory, that increased pressure results in higher batch temperature which in turn impacts supersaturation and the point at which crystallization commences in an unseeded batch. It was determined that higher pressure results in crystallization later in the batch cycle than for lower pressure batches, with the result being a negative impact on cake permeability and reduced ability to wash impurities from the cake. For instance, in unseeded operations a wetcake permeability range of $1 \times 10^{-8}$ to $1.6 \times 10^{-8}$ cm² and a chloride concentration of about 500 ppm to about 3000 ppm are typically associated with PM operating pressures of about 15 psig (2.1 kg/cm² absolute) to 20 psig (2.4 kg/cm² absolute). In seeded operations, PM reactor pressures of about 25 psig (2.7 kg/cm² absolute) are attainable without a concomitant wetcake permeability decrease or chloride content increase. Commercial scale testing further indicates that seeding at about 2 wt % can increase wetcake permeability by at least about 30% without significant changes to crystal morphology and process chemistry.

Increased crystal bed permeability has also been found to be associated with decreased agitation speed in the PM reactor. Commercial scale data indicate that crystal bed (i.e., wetcake) permeability may be increased by as much as about 20% when the PM reactor agitation speed is halved. In general, the agitation rate should be sufficient to overcome pockets of local supersaturation, but insufficient to cause excessive crystal breakage and concomitant secondary nucleation.

High wetcake permeability advantageously maximizes dewatering capabilities and ease of impurity removal from the crystal by washing thereby reducing cycle times and enabling higher throughput through solid-liquid separation equipment. The increased washing efficiency also accrues the additional benefit of reduced wash water requirements thus minimizing PMIDA losses into spent mother liquor.

The prior art PMIDA processes typically operate at about 95% yield. Although those yields are high, significant cost and environmental benefits could be achieved by increasing the yield. It has been discovered that crystallization kinetics, formed crystal morphology and crystal purity may be optimized to further increase the yield. It has further been discovered that by altering the PMIDA crystal size distribution and purity in order to improve solid-liquid separation performance, additional significant increases in yield may be achieved.

Experimental evidence to date also indicates that seeding lowers the amount of residual PMIDA left in the mother liquor, and thus improves the yield of PMIDA crystals during commercial scale operations. Without being limited to a particular theory, it appears that seeding effectively reduces the supersaturation of PMIDA remaining in the mother liquor after completion of the batch steps (i.e., reaction, cooling, and holding the cooled slurry for a finite period of time). That is, the extent of the reduction in supersaturation (i.e., shedding) over a finite period of time is favorably affected by seeding. Accordingly, PMIDA seeding provides improvements in yield at comparable cycle times. Several factors could be responsible. For instance, as compared to non-seeded systems, crystallization is initiated earlier and at lower supersaturation thereby providing additional time for the crystals to form. Additionally, since the supersaturation at the start of crystallization in seeded systems is lower than in non-seeded spontaneous nucleation, the degree of supersaturation remaining in the mother liquor after the reaction is completed and cooling to the desired temperature is also lower.

Crystal morphology and purity optimization accrues the benefit of reducing wash water volumes per unit weight of PMIDA because porous crystal beds enable efficient mother liquor, hence impurity, removal, and allows efficient crystal washing. Wash water removes impurities but also solubilizes PMIDA that is either recycled or lost as waste. Minimizing wash water volume requirements thereby reduces PMIDA loss and increases yield.

It is known to those in the art that solution viscosity is generally inversely proportional to temperature. The dependence of filtration rate on the applied pressure phenomena is described by Darcy's law: a mathematical description of liquid flow through porous media wherein media permeability, hence liquid flow and dewatering capability, varies inversely with fluid viscosity. In other words, Darcy's law provides a mathematical characterization of the relationship between the flow rate of filtrate and the driving force applied. It is usually expressed as Equation 1.4, where Q is the flow rate, K is the permeability, A is the filtration area, $\Delta P$ is the pressure drop, $\mu$ is the filtrate viscosity, and L is the cake thickness.

$$Q = KA\Delta P/\mu L \quad (1.4)$$

Because, in part, of the negative impact of increased viscosity on crystal bed permeability, thus dewatering rate, the prior art crystallization temperature is typically limited to a minimum of about 50° C. Under the practice of the present invention, adequate dewatering rates may be achieved at temperatures as low as about 40° C. without significant impact on PMIDA quality or rate of manufacture. Moreover, lower temperature operation results in reduced loss of solubilized PMIDA to the mother liquor and wash water.

Efficient dewatering also enables PMIDA drying cost savings to be realized. For example, because the PMIDA moisture content is low, drying times are reduced thereby enabling cycle time reductions with concomitant throughput increases and energy savings. Further, a reduction in the number of fines increases yield because less PMIDA is lost through dryer dust collection equipment such as baghouses or cyclones. Moreover, a lower percentage of crystal fines enables dust collection equipment to operate more efficiently by decreasing blinding, hence reducing pressure drop across dust collection filters.

Seed crystals may be introduced into the PM reactor in a variety of ways. For example, as in FIG. 1, solid PMIDA seed may be added to the PM reactor by a dry solid feeding system that charges a weighed quantity of material to the reactor through a mechanism such as a rotary valve or a sealed chamber that isolates the reactor from the environment during charging thereby maintaining PM reaction pressure. In another seed charging method depicted in FIG. 1, a fixed volume of crystal slurry from the crystallizer tank can be recycled back to the PM reactor as seed crystals.

In a first embodiment of the present invention, seeding is done at relatively high PMIDA σ values in order to minimize the amount of fines produced and thereby maximize formed crystal bed permeability and dewatering rate. High supersaturation driving force is present at elevated σ values resulting in rapid relaxation (i.e., "shedding") of the supersaturation concentration within the metastable zone. Thus, following seeding, a fast initial crystal growth rate results followed by a slower post-relaxation growth rate as the concentration is maintained in the supersaturation metastable zone by PMIDA formation as the reaction proceeds. Moreover, because crystallization is initiated at a lower supersaturation than spontaneous nucleation, the initial bulk crystallization rate is lower than with spontaneous nucleation. As compared to PMIDA crystals known in the art, the morphology of the PMIDA crystals prepared under this embodiment is generally characterized by larger crystals of higher purity and a relative absence of fine crystals resulting in formed crystal beds of high permeability, filtration rate, and porosity. In this embodiment, the formed crystal median chord length (as measured using a Lasentec® FBRM® D600 Crystallization Monitor, described infra) is about 10% larger than crystals formed in a comparable, but unseeded, process. Similarly, crystal bed permeability can be increased by at least about 20% over unseeded processes. Additionally, crystal bed porosity can also be increased by about 10% over comparable, but unseeded, processes. According to this process alternative, to minimize the amount of fines and thereby prepare crystals that form permeable packed beds, it is preferred to seed the PM reactor at a σ value greater than about 1, preferably between about 1 and about 2, more preferably between about 1.5 and about 2. It is generally desirable to seed just prior to the point of maximum supersolubility in order to have a high supersaturation driving force.

Balanced against the permeability advantages of the first seeding option is the inclusion of impurities as promoted by the fast crystal growth rate which results, for example, from the primary and secondary inclusion mechanisms previously discussed. It is to be noted however that impurity concentrations and the impurity partitioning coefficient, even for crystals prepared by seeding at the maximum supersaturation concentration, or a $\sigma_{max}$ of about 2, are generally reduced by comparison with those found in PMIDA crystals prepared in unseeded systems. Moreover, high bed permeability permits more efficient mother liquor removal and purification by washing thereby providing enhanced removal, as compared to unseeded systems, of included impurities associated with this embodiment.

According to another process alternative, seeding is done at relatively low PMIDA σ values in order to minimize the amount of impurities included in the formed crystal and thereby maximize PMIDA yield. Supersaturation driving force is relatively low at reduced σ values resulting in a slow, controlled, relaxation of the supersaturation concentration within the metastable zone. Thus following seeding, a relatively low initial crystal growth rate results followed by a lower post-relaxation growth rate as the concentration is maintained in the supersaturation metastable zone by PMIDA formation as the reaction proceeds.

The controlled PMIDA crystal growth rate of this embodiment promotes higher crystal purity. Reductions in the impurity partitioning coefficient of about 5%, 10%, and as high as about 15% are achievable as compared to unseeded processes. For example, as compared to unseeded processes, NMG crystal bed concentration reductions of as much as about 10% (on an NMG basis) can be attained. To minimize the amount of included impurities and maximize PMIDA yield, it is preferred to seed the PM reactor at a σ value less than about 1, preferably between 0 and about 0.5, between 0 and about 0.3, between 0.1 and about 0.3, and still more preferably between about 0.2 and about 0.3.

Balanced against the crystal purity advantages of this embodiment is decreased crystal bed permeability resulting from slow crystal growth rates as compared to seeding at relatively high PMIDA σ values. It is to be noted however that permeability, even for crystals prepared by seeding at the minimum supersaturation concentration (e.g., σ of about 0 to about 0.1) can be increased by over 10%, for example about 15%, over PMIDA crystals prepared in unseeded systems. Moreover, lower levels of included impurities reduce mother liquor removal and purification requirements thereby at least partially obviating any permeability disadvantages associated with this embodiment. Additionally, for σ values less than about 0.3, lower seed crystal amounts, such as less than about 4 wt %, 3 wt %, 2 wt %, 1.5 wt % or 1 wt %, can be added to the PM reactor in order to fix the number of crystals at a lower number thereby enabling larger crystals to be prepared.

According to a third process option, seeding is done at intermediate PMIDA σ values in order to obtain the benefits of both minimizing impurity inclusion and improving PMIDA wetcake bed porosity. In this case, it is preferred to seed the PM reactor at a σ value between about 0.5 and about 1.5, between about 0.7 and about 1.5, more preferable between about 1 and about 1.5. Thus, glyphosine partitioning to the PMIDA wetcake can be reduced by as much as about 15% and NMG wetcake concentration can be reduced by as much as about 10% over comparative, unseeded processes, while concomitantly generating PMIDA wetcake exhibiting enhanced permeability over PMIDA prepared in unseeded processes. Advantageously, crystal bed permeability increases over unseeded processes of 10%, 15%, 20% and as high as about 25% can be achieved.

In accordance with a still further option, seeding may be done at a σ specifically selected to meet the crystal purity, bed permeability, or a combination of purity/permeability requirements unique to individual PMIDA processes in order to optimize throughput, quality and cost. For example, high impurity concentrations in feeds can be compensated for without significant adverse impact on throughput or quality. Further, in some commercial processes, PMIDA preparation and crystallization capacity may exceed dewatering and washing capacity thereby creating a process bottleneck in solid-liquid separation operations. In that case it may be advantageous to seed at relatively high σ values wherein a very porous crystal bed is formed, thus increasing throughput without additional capital investment. Conversely, a process bottleneck could be caused by lack of PMIDA preparation tankage or intermediate process storage. Throughput optimization could require a faster reactant addition sequence at the expense of higher impurity generation. In that case it would be advantageous to seed at σ values wherein crystal purity is improved. As a third case, overall throughput could be increased by seeding at an intermediate σ value thereby optimizing both the benefits of a crystal with enhanced purity and formed bed porosity. Advantageously therefore, PMIDA seeding allows needs-based selective purity and throughput optimization and builds in process flexibility to enable the effects of interruptions such as equipment failure, varying impurity contamination, etc. to minimized.

In accordance with another process option, process feed interruption can be employed in lieu of seeding. In this option, an unseeded PMIDA batch is monitored for initiation of crystallization. Suitable indicators of crystallization onset include, for example, a change in reaction solution optical properties such as an increase in turbidity or light absorbance, decrease in light transmission, increase in batch viscosity, or increased agitator power consumption. When crystallization initiation is detected, the reaction feeds can be interrupted thereby allowing a slow, controlled relief of supersaturation. Feed interruption includes feed stoppage or a decrease in feed rate in a step-wise and/or linear fashion. In one embodiment of this process option, the feeds are stopped for a predetermined amount of time or until a particular value of an indicator, such as turbidity or light transmission, is achieved. In another embodiment, feed rates are decreased to a predetermined value in a step-wise fashion or in a controlled manner in accordance with, for example, a programmed feed ramping rate or a process control feed rate loop with the feed rate setpoint determined and set by a measured indicator such as turbidity. Such process control schemes are well known in the art.

It has been discovered that feed stoppage or interruption can also result in reduced glyphosine levels. In particular, based on the observed kinetics for glyphosine and NMG formation, NMG formation appears as an asymptotic curve and is produced at a greater relative rate than is glyphosine which exhibits a linear rate of generation. Under one theory, it is proposed that because the formation of glyphosine requires two moles of formaldehyde (i.e., formalin), feed interruption or stoppage results in a formalin depletion with a reduction in the amount of formalin formed glyphosine as compared to NMG. Thus feed interruption or stoppage after the crystallization event will have more of a relative impact on glyphosine partitioning.

In any of the various embodiments, selective seeding can be coupled with formalin feed interruption (or stoppage) or a stepped down formalin feed rate in order to further optimize impurity reduction in PMIDA wetcake. In the case of seeding at low σ values, formalin feed interruption has been found to be particularly effective in reducing impurity levels in PMIDA wetcake. By that method glyphosine partitioning to the PMIDA wetcake can be reduced by as much as about 25% (on a weight percent basis) and NMG wetcake concentration can be reduced by as much as about 15% (on a part per million percent basis) as compared to comparative, unseeded processes. A feed stoppage of at between about 5 minutes and about 30 minutes is preferred. Alternatively, the formalin feed rate can be stepped down after seeding.

The present invention is applicable to processes for the preparation of any material whereby material generation and crystallization occur simultaneously. In particular, the discoveries enable efficient preparation of such compounds by allowing the reactions of such processes to be run at supersaturation concentration without the risk of uncontrolled crystallization, heretofore not achievable in the absence of seeding during the reaction step. Moreover, the present invention allows optimization of formed crystal morphology and material purity for those materials.

The following examples are simply intended to further illustrate and explain the present invention. This invention, therefore, should not be limited to any of the details in these examples.

EXAMPLES

The mechanism of impurity incorporation into the PMIDA cake was evaluated. Repeated washing of the cake has shown that while a portion of the impurities was located at or near the crystal surface, the remainder could be accessed only by dissolving the crystals.

Crystal sieving experiments were performed to investigate if impurity concentration varies with crystal size. Impurity concentrations have been shown to trend upward at very large crystal sizes, while those concentrations remain relatively constant at smaller size, suggesting that impurities are incorporated into the crystal during growth. It is believed that impurities have to be ejected through the boundary layer positioned at the interface between the growing crystal and the surrounding process liquid, and if the crystal is growing at a faster rate than the rate at which the impurities are rejected then greater amounts of impurities become trapped within the crystal.

Controlled cooling crystallization experiments were done to determine if controlling the crystal growth rate could be used to limit the extent of impurity partitioning to the PMIDA cake. Those experiments were also used to determine a lower bound on impurity partitioning that could be achieved in the absence of constraints on cycle time.

Two sources of DSIDA, termed DSIDA1 and DSIDA2, were used in the experiments. DSIDA1 contained about 0.3% sodium glycinate impurities. DSIDA2 contained about 0.5% sodium glycinate and about 0.3% sarcosinate impurities.

Experiments were varied according to seeding times and/or amounts, impurity levels at time of the crystallization event (i.e., "crash event"), feed stoppages, agitation rates and stepped formalin feeds. Stepped formalin refers to the reduction in formalin feed rate later in the batch in order to extend the time available for crystallization. Seeding amounts ranged from 2% of the total final batch weight to 4% of the final batch weight. Seeding start times ranged from early seeding (after about 30% of the total formalin addition) to late seeding (after about 50% of total formalin addition). In some experiments that used DSIDA1 feed, an NMG "spike" of up to about 0.55% of the final batch weight was added to test for the impact of NMG levels on its partitioning and to test for any impact on filtration.

PM reaction experiments were performed under a variety of conditions. In one series of evaluations, baseline, or comparative, experiments were performed for three different process conditions representing those typically encountered in commercial practice of the present invention.

It was found that levels of glycine varied in DSIDA1 samples taken from the same lot, which led to varying wetcake glyphosine concentrations. Thus, to reduce variability in the analyses, instead of measuring actual concentration, evaluations of glyphosine incorporation into the PMIDA cake were determined by calculating the percentage that partitioned to the cake. NMG reductions were assessed on actual concentrations in the cake rather than partitioning percentages because the amounts of NMG spiked were constant thereby providing consistent results.

Experiments were done in a two-piece 1000 mL glass reactor supplied by Ace Glass, Inc. Two aftermarket glass baffles were installed to mimic manufacturing plant equipment. The reactor had four #15 ports and one #25 port. The #25 port was used for charging and sampling, and was fitted with a pH probe for neutralization steps. A J-type thermocouple was inserted into one of the #15 ports. The thermocouple was connected to a series 16A Love controller, which regulated the power supply to a Glas-Col heating mantle rated at 335 watts. Because the reactor had a drain port to enable easy recovery, the bottom of the heating mantle was open. A glass agitator shaft was inserted through the center #15 port. Agitation was regulated by a Servodyne mixer head and controller. A rotating flex-shaft connected the mixer heat to a coupling adapter, to which the agitation shaft was attached. A turbine Teflon impeller was attached to the agitator shaft approximately 0.6 cm from the bottom of the reactor. Impeller blades were about 2 cm in wide and 2.5 cm high. A tee was attached to one of the #15 ports to allow the use of that port for both a condenser and a DSIDA feed line. Cooling water for the condenser was supplied by laboratory utilities and was generally slightly lower than ambient temperature. Rubber tubing ran from the top of the condenser to the water scrubber where reaction gas was scrubbed. A $PCl_3$/formalin feed line was placed through the final #15 port. Both feed lines were made of ⅛ inch (0.32 cm) PTFE tubing and were long enough such that they reached the impeller blades.

Two Masterflex Easy-load series 7518-00 peristaltic pumps transferred material from feed bottles to the reactor via the feed lines. Both pumps used viton tubing which was connected to feed bottles and the reactor feed lines. The first pump was dedicated to DSIDA addition and the second pump was dedicated to $PCl_3$ and formalin addition, however, each had a dedicated feed line. To prevent crystallization, the DSIDA and formalin feed bottles and feed lines were heated using two Glas-Col power amplifiers. The feed bottles were placed on balances in order to accurately measure feed rate and total feed added. As the hydrolysis and PM steps were done, feed amounts were tracked by noting the weight of feed that had been removed from each bottle.

Before each hydrolysis step the reactor was thoroughly cleaned with a dilute sodium hydroxide solution followed by several deionized water rinses. After cleaning, all ports were sealed, the heating mantle was placed on the reactor, and the reactor was preheated. DSIDA feed was then charged into the reactor and agitation started. The $PCl_3$ feed bottle was then filled and closed, and the $PCl_3$ feed line was attached to the bottle and the reactor feed port. The $PCl_3$ feed line contained a check valve to prevent backflow of the reactor contents into the feed bottle. Following DSIDA addition, the reactor temperature was increased to about 95° C. and the $PCl_3$ feed was then started and charged into the reactor at a fixed rate. After $PCl_3$ feed completion the feed line was cleared by blowing forward to the reactor with nitrogen.

Following the DSIDA hydrolysis reaction, the PM reaction sequence was performed to yield PMIDA. If the PM reaction was spiked with impurity, the glyphosine and/or NMG impurities were added to the reactor through the charging port. The spike, if used, as well as any buildup on the reactor walls was washed down using a measured amount of deionized water. Appropriate amounts of DSIDA and formalin feeds were added to pre-heated feed bottles, the bottles were tared, and the DSIDA and formalin feeds to the reactor were started. Following reaction completion, each feed line was flushed forward to the reactor with about 10 grams of deionized water. The reactor was then held for about an hour at about 105° C. to drive the reaction to completion.

After the hold period, slurry cooling was initiated. During the cooling step, dilution water was added at a temperature between about 85° C. and about 90° C. Neutralization using an online pH probe was done using sodium hydroxide when the temperature was between about 65° C. and about 70° C. The slurry was cooled to about 50° C. and held at that temperature for about 30 minutes.

Following the hold period, a standard permeability test was then performed on the warm slurry to measure the percent solids present in the slurry and to determine the permeability of the solids. In this test, a standard filtration apparatus consisting of a Whatman 210 mL slurry reservoir, #1 Whatman filter paper (70 mm) placed on a perforated disk and a measuring cylinder adapter was assembled and tared. The filtration apparatus was connected to a tared measuring cylinder having a port connected to a vacuum pump set to provide a vacuum of about 5 inches of mercury (about 127 mm Hg). About 200 mL of a sample was vigorously shaken and placed in a tared 250 mL beaker. The total weight, volume and temperature of the sample was measured and recorded. The vacuum pump was started and the sample was stirred and then poured into the vacuum filtration apparatus at time zero. Filtration times were recorded at 10 mL intervals of filtrate volume. The end time was measured when the last portion of slurry was drawn into the formed filter cake (the "dry land point"). "Dry land" filtration volume was measured and recorded. Vacuum was maintained for 5 minutes after which the vacuum was broken and the cake height was then measured and recorded. The filtration apparatus and measuring cylinder were disconnected and the filtrate was transferred from the collection cylinder to a sample bottle after which the cylinder was washed, dried and re-tared. The filtration apparatus and measuring cylinder were reconnected and vacuum was reestablished. At zero time an amount of deionized water equal to 60% by weight of the wetcake weight was measured, recorded and added to the filtration apparatus. Filtration times were recorded at 10 mL intervals of filtrate volume. The end time was measured when the last portion of wash water was drawn into the formed filter cake (i.e., the "dry land" point). Vacuum was maintained for 5 minutes after which the vacuum was broken and total wash water volume, cake weight, filtrate weight and total time were then measured and recorded. The filtration apparatus and measuring cylinder were disconnected and the wash water filtrate was transferred from the collection cylinder to a sample bottle. The loss on drying ("LOD") of the washed wetcake was measured and recorded. The wetcake was retained for further analysis.

From the standard permeability test results, slurry and filtrate specific gravity, percentage of solids in the slurry, and a modified filtration rate (in mL·cm/min) were calculated. The modified filtration rate is filtration rate multiplied by cake thickness and is an estimate of permeability.

The standard permeability test results were entered into a filtration rate data analysis program, FDFit, available from Aspen Technology Inc. The program fits a curve to the filtrate volume versus time data collected until the point at which the last liquid touched the wetcake ("dry land point") and calculates the cake permeability and its reciprocal (the cake resistance) based on the volume of the filter cake. Permeability was found to vary with the type of filter paper used (i.e., degree of filter paper resistance), cake thickness and cake moisture. However, through the use of a standardized permeability test the standardized method, above, repeat tests on the same sample indicate that the overall variability can be limited to about 6%.

The slurry particle size distribution was measured to determine the median particle size and to measure the total number of particles in the batch. That measurement was done using a Lasentec® FBRM® (focused beam reflectance measurement) D600 Crystallization Monitor, available from Laser Sensor Technology Inc. of Redmond, Wash., USA. The FBRM® Chord Length Distribution is a number based measurement and provides particle counts ranging 1.0 to 1000 microns. A highly focused laser beam is projected through the probe sapphire window and, at a fixed velocity, rapidly scans across particles and particle structures flowing past the probe window. When the focused beam intersects the edge of a particle, the particle will begin to backscatter the light. The particle will continue to backscatter until the focused beam has reached the opposite edge of the particle. The backscatter is collected by the FBRM® optics and then converted into an electrical signal. A unique discrimination circuit is used to isolate the period of the backscatter from one edge of an individual particle to its opposite edge. That period is multiplied by the scan speed to calculate a distance, that distance being the chord length. A chord length is a straight line between any two points on the edge of the particle or particle structure (e.g., agglomerate). Hundreds of thousands of chords can be measured per second that results in a number by chord length distribution (i.e., number of counts per second sorted by chord length into 1000 linear size bins).

HPLC was used to measure the levels of PMIDA, glyphosine, NMG, etc., as reported in the Examples that follow. Analysis was performed using Varian instruments (pumps, lamps, etc.) that used ionic chromatographic columns.

Comparative Example 1

This example investigated the relationship between PMIDA crystal size and observed glyphosine and NMG impurity levels. The PMIDA was prepared from DSIDA2 without seeding. Mean particle size was derived from sieve size analysis. Glyphosine and NMG concentrations were measured by HPLC. The results are reported in Table 1.

TABLE 1

| Mean PMIDA crystal size (microns) | glyphosine (wt %) | NMG (ppm) |
|---|---|---|
| 638 | 1.20 | 4484 |
| 338 | 1.16 | 3838 |
| 200 | 1.03 | 4216 |
| 113 | 1.03 | 3741 |
| 60 | 1.01 | 3805 |
| 23 | 1.04 | 3814 |

The data show that impurity levels tend to increase with mean crystal size. This trend suggests impurities are incorporated within the growing crystalline structure during the crystal growth phase.

Comparative Example 2

This example investigated the effect of repeated washing on PMIDA purity. The PMIDA was prepared from DSIDA2 without seeding. In a first wash, approximately 10 grams of PMIDA wetcake was added to about 90 grams of water and allowed to mix for about ½ hour at room temperature. The wash 1 liquid was filtered off leaving behind about 14 grams of wetcake. The PMIDA, glyphosine and NMG concentrations in the wash 1 liquid was determined by HPLC. This process was repeated five more times to generate results for the wash 2 through wash 6 liquids. After the sixth wash the resultant wetcake was dried and analyzed. The results are reported in Table 2A below.

TABLE 2A

Results from repeated washing of PMIDA

| Sample | PMIDA (wt %) | glyphosine (wt %) | NMG (ppm) | glyphosine/ PMIDA | NMG/ PMIDA |
|---|---|---|---|---|---|
| Crude PMIDA | 97.9 | 1.279 | 4544 | 0.013 | 46.4 |
| Wash 1 | 0.660 | 0.056 | 174 | 0.085 | 263.6 |
| Wash 2 | 0.661 | 0.013 | 47 | 0.020 | 71.1 |
| Wash 3 | 0.669 | 0.009 | 35 | 0.014 | 52.3 |
| Wash 4 | 0.676 | 0.008 | 5 | 0.012 | 7.4 |
| Wash 5 | 0.683 | 0.008 | 5 | 0.012 | 7.3 |
| Wash 6 | 0.719 | 0.008 | 11 | 0.011 | 15.0 |
| Dried PMIDA | 99.5 | 0.849 | 2877 | 0.009 | 28.9 |

The wash 6 results are questionable due to HPLC analysis difficulties. The results indicate that repeated washing does increase wetcake purity, but some impurities remain after repeated washing, implying that the impurities are also incorporated throughout the crystal structure. But, while it appears that impurities are incorporated throughout the crystal, the data indicate that a greater proportion are present at the outer portion of the crystal. 67% of the total glyphosine and 73% of the total NMG removal occurred during wash 1, when only the outer portions of the PMIDA crystal were dissolved.

Two additional experiments were performed to investigate impurity removal with respect to wash residence time and PMIDA concentration. In both experiments the PMIDA was prepared from DSIDA2 without seeding.

In the first experiment, to test the impact of residence time, about 10.0 grams of unwashed PMIDA were placed in about 100 grams of deionized water and mixed for about 2 minutes before the water was filtered off and collected. To test the impact of PMIDA concentration, about 90.0 grams of PMIDA were placed in about 90 grams of deionized water and allowed to mix for about 30 minutes before the water was filtered off and collected. The results are presented in Table 2B.

TABLE 2B

First wash sample analyses from PMIDA washing experiments

| | Repeated washing test | Residence time test | PMIDA concentrate test |
|---|---|---|---|
| water/wetcake (g/g) | 10/90 | 10/90 | 90/90 |
| mixing time (min) | 30 | 2 | 30 |
| PMIDA wt % | 0.66 | 0.62 | 0.54 |
| glyphosine wt % | 0.056 | 0.060 | 0.39 |
| NMG ppm | 174 | 181 | 1412 |

The data of Table 2B indicate that decreasing the residence time does not appear to affect the amount of impurity removed, but altering the wetcake concentration greatly affects the amount of impurity removed. By significantly increasing the wetcake concentration in the slurry, a smaller amount of each PMIDA crystal is dissolved. This finding supports the conclusion that the PMIDA crystals have an impurity profile with the impurity concentration decreasing with distance from the crystal surface.

The data presented in Table 2C were calculated from the weight and analysis of filtrate recovered in each experiment, with wetcake charge rates and the initial PMIDA wetcake composition as noted in Table 2B.

TABLE 2C

Comparison of impurity reductions observed in washing DSIDA2-based PMIDA

| | Repeated washing test | Residence time test | PMIDA concentrate test |
|---|---|---|---|
| wetcake PMIDA purity after wash (wt %) | 98.8 | 98.8 | 98.6 |
| glyphosine in wetcake after wash (wt %) | 0.86 | 0.84 | 1.07 |
| NMG in wetcake after wash (ppm) | 3282 | 3249 | 3777 |
| % PMIDA lost in wash | 5.74 | 5.24 | 0.31 |
| glyphosine % reduction in wetcake | 32.7 | 34.7 | 16.4 |
| NMG % reduction in wetcake | 27.5 | 28.5 | 16.9 |

From the data, glyphosine is more easily removed by washing than NMG, suggesting that less NMG is on the crystal surface. While reductions of about 34% in wetcake glyphosine concentration and about 28% in wetcake NMG concentration are attainable, associated PMIDA losses with the required wash water volume are high. By washing with lower volume of water, PMIDA losses are decreased, and reductions of impurity concentrations are approximately halved.

In Examples 3, 4 and 5 that follow, three basic types of unseeded baseline, or comparative, PMIDA preparation processes were characterized. The first baseline example used DSIDA1. The DSIDA1 and formalin were fed at a linear rate over about 50 minutes with no DSIDA1 or formalin feed stoppages. The second baseline example used DSIDA2. DSIDA2 and formalin feed times were 60 minutes and 65 minutes, respectively, and the formalin feed was stepped down for about 20 minutes. Both the first and second baseline experiments used a molar excess of 10% for $PCl_3$ and 19% for formalin. The third baseline example used DSIDA1, had linear feed times, without feed stoppages, of 60 minutes and 65 minutes for DSIDA1 and formalin, respectively. The $PCl_3$ molar excess was decreased to 8.5%.

Example 3

A first set of comparative PMIDA experiments were done without seeding to establish a baseline from which the effects of PMIDA seeding could be evaluated. The experiments were done using 43% formalin feed as the formaldehyde source. One preparation used a stepped-formalin feed. The experiments were done to enable evaluation of the impact of seeding, to determine the impact of NMG on overall impurity partitioning, and to evaluate the effect of stepped-formalin feed on impurity partitioning.

PM run 1 evaluated the effect of elevated NMG levels on glyphosine partitioning and established a reference for comparing varying types of seeding experiments. After the hydrolyzer step was completed, 0.56% on a final batch weight basis of NMG was added to the reactor. Total feed times were 55 minutes for DSIDA1 and 60 minutes for formalin. PMIDA appeared to crash from solution after about 63% of the total formalin had been added. Table 3A gives the results of ML sample analysis for samples taken during the PM reaction sequence and prior to cooling. Table 3B lists the NMG and glyphosine concentrations and partitioning percentage for the final recovered components. The term "final components" refers to products produced by filtering the PM reaction product, thus leaving a wetcake and ML. The wetcake was then washed with water which was collected and labeled as "wash," and the resulting wetcake was dried. The term "partitioning %" refers to the relative amount of impurity in the wetcake and is calculated by dividing the amount of impurity (i.e., NMG or glyphosine) which is present in the wetcake by the total amount of impurity present in the wetcake, mother liquor and wash.

TABLE 3A

Mother liquor compositions from PM run 1

| Sample | Time after start of formalin feed (min) | PMIDA (wt %) | glyphosine (wt %) | NMG (ppm) |
|---|---|---|---|---|
| ML 1 | 20 | 15.2 | 0.13 | 8365 |
| ML 2 | 25 | 18.0 | 0.11 | 8489 |
| ML 3 | 30 | 19.9 | 0.15 | 7802 |
| ML 4 | 43 | 15.4 | 0.21 | 6974 |
| ML 5 | 68 (addition complete - start of hold) | 6.4 | 0.25 | 5575 |
| ML 6 | 123 (end of hold) | 5.6 | 0.37 | 5935 |

TABLE 3B

Final component impurity analyses from PM run 1

| Component | glyphosine (wt %) | NMG (ppm) | glyphosine partitioning (%) | NMG partitioning (%) |
|---|---|---|---|---|
| ML | 0.23 | 4124 | — | — |
| Wash | 0.11 | 1994 | 37.6 | 26.1 |
| Dried Cake | 0.48 | 5192 | — | — |

PM run 2 evaluated the effect of NMG on impurity partitioning and determined if varying the NMG concentration affects glyphosine and NMG partitioning. After the hydrolyzer step was completed, about 0.1% on a final batch weight basis of NMG was added to the reactor. Total feed times were 50 minutes for both DSIDA1 and formalin. Neither seeding nor a stepped-formalin feed was done. Table 3C gives the NMG and glyphosine concentrations and partitioning percentages for the final recovered components.

TABLE 3C

| Component | glyphosine (wt %) | NMG (ppm) | glyphosine partitioning (%) | NMG partitioning (%) |
|---|---|---|---|---|
| ML | 0.37 | 1080 | — | — |
| Wash | 0.12 | 506 | 30.0 | 24.8 |
| Dried Cake | 0.53 | 1191 | — | — |

PM run 3 evaluated the effect of NMG on impurity partitioning for 50 minute DSIDA1 and formalin feed times, without seeding or stepped-formalin feed, and without added NMG. Table 3D gives the glyphosine concentrations in wt % and glyphosine partitioning percentages. Only trace amounts of NMG were found.

TABLE 3D

Final component glyphosine analyses for runs 3A and 3B

| Run ID | ML glyphosine | Wash glyphosine | Wetcake glyphosine | glyphosine partitioning |
|---|---|---|---|---|
| Run 3A | 0.24 | 0.064 | 0.40 | 33.3 |
| Run 3B | 0.19 | 0.060 | 0.30 | 31.6 |

PM run 11 was done to establish a baseline for DSIDA1 feeds in which stepped feeds but no seeding were used. Following the hydrolysis step, about 0.55% on a final batch weight basis of NMG was added to the reactor. The DSIDA1 feed time was about 60 minutes and the formalin feed time was about 65 minutes. Table 3E gives the PMIDA concentration (wt %) in the slurry and mother liquor versus percent formalin added.

TABLE 3E

| % formalin added | Slurry PMIDA (wt %) | ML PMIDA (wt %) |
|---|---|---|
| 33% | 11.3 | 13.4 |
| 48% | 16.8 | 19.1 |
| 61% | 19.3 | 21.8 |
| 75% | 21.7 | 22.5 |
| 100% | 23.8 | 10.1 |

The data of Table 3E indicate that crystallization began at about 70% of total formalin addition. Based on data interpolation it appears that the ML reached a PMIDA concentration of about 24.0% before crystallization occurred. The PMIDA wt % value at 100% formalin addition was measured after the formalin addition was complete and the batch was cooled.

The final components of run 11 were analyzed for purity with the results reported in Table 3F.

TABLE 3F

| Component | glyphosine (wt %) | NMG (ppm) | glyphosine partitioning (%) | NMG partitioning (%) |
|---|---|---|---|---|
| ML | 0.20 | 4363 | — | — |
| Wash | 0.10 | 1982 | 35.9 | 24.3 |
| Dried Cake | 0.41 | 5036 | — | — |

The baseline experiments indicate that the adding NMG to the reactor altered the final wetcake concentrations but the NMG partitioning percentage was relatively unaffected suggesting that the mechanism behind NMG incorporation is independent of its concentration.

The baseline experiments indicate that varying NMG concentrations slightly increased the glyphosine partitioning percentage. The average glyphosine partitioning percentage for runs where a NMG spike of 0.1% on a final batch weight basis was added to the PM reactor was 31.6%, while the average increased to 36.8% for runs containing a NMG spike of 0.55% on a final batch weight basis. Under one theory, and without being bound to any particular theory, because glyphosine is more easily washed from PMIDA than is NMG, an ineffective washing step could result in a cake with higher glyphosine levels.

Finally, a stepped formalin feed addition did not significantly decrease the partitioning percentages of glyphosine or NMG.

Example 4

A second set of comparative PMIDA experiments was done without seeding to establish a baseline from which the effects of PMIDA seeding could be evaluated. The experiments were done using DSIDA2 and 43% formalin feed, and the formalin feed was stepped down. The feed DSIDA2 and formalin feed times for run 9 were 65 and 70 minutes, respectively, and for run 10 were 60 and 65 minutes, respectively. In run 9 the formalin feed rate was stepped down, or dropped by about one third, after about 33% of the total formalin had been added while in run 10 the formalin feed rate was stepped down, or dropped by about one third, after about 38.5% had been added. Crystallization onset was observed at about 61% of total formalin addition in run 9 and at about 67% of total formalin addition in run 10. The results are reported in Tables 4A to C below.

TABLE 4A

PM run 9 ML composition profile

| % formalin added | PMIDA (wt %) | NMG (ppm) | glyphosine wt % |
|---|---|---|---|
| 24% | 14.9 | 3855 | 0.22 |
| 41% | 18.2 | 4527 | 0.24 |
| 49% | 20.6 | 3812 | 0.32 |
| 56% | 22.3 | 4794 | 0.36 |
| 59% | 23.7 | 4531 | 0.36 |
| 72% | 13.1 | 4719 | 0.42 |
| 100% | 5.9 | 4528 | 0.45 |

TABLE 4B

PM run 9 slurry composite profile

| % formalin added | PMIDA (wt %) | NMG (ppm) | glyphosine wt % |
|---|---|---|---|
| 24% | 12.3 | 3122 | 0.18 |
| 41% | 15.4 | 3916 | 0.20 |
| 49% | 17.5 | 4123 | 0.23 |
| 56% | 19.2 | 4166 | 0.24 |
| 59% | 22.5 | 4675 | 0.34 |
| 72% | 22.8 | 4043 | 0.36 |
| 100% | 24.9 | 4082 | 0.43 |

TABLE 4C

PM run 10 ML composition profile

| % formalin added | PMIDA (wt %) | NMG (ppm) | glyphosine wt % |
|---|---|---|---|
| 25 | 13.3 | 3684 | 0.14 |
| 38 | 17.1 | 4193 | 0.15 |
| 44 | 19.4 | 4481 | 0.21 |
| 51 | 20.9 | 4585 | 0.24 |
| 57 | 22.3 | 4689 | 0.27 |
| 70 | 23.2 | 4780 | 0.35 |
| 79 | 15.1 | 4616 | 0.35 |
| 100 | 8.9 | 5072 | 0.44 |

The data of Tables 4A to 4C indicate that NMG production is more rapid than glyphosine production. The data further indicate that the majority of the NMG production occurs before crystallization while glyphosine production occurs throughout the entire PM step as well as the hold step. The data imply that the point of onset of PMIDA crystallization is more important to NMG partitioning than to glyphosine partitioning and that slowing or stopping formalin feeds after the crystallization event will have more of a relative impact on glyphosine partitioning. That conclusion is based on the kinetic observation that glyphosine formation is faster than NMG formation. It is believed that the formation rate is influenced by the fact NMG requires one mole of formaldehyde, while formalin formation requires two moles. Therefore, after the formalin feed is slowed or stopped formalin is depleted with the ovserved result being reduction in the ratio of formalin to NMG, or a relative reduction in glyphosine formation.

The data of runs 9 and 10 were used to establish baseline values of impurity concentrations and partitioning percentages in the collected DSIDA2-based PMIDA cake and mother liquor. The results are reported in Table 4D.

TABLE 4D

Final component analyses from process baseline runs 9 and 10

| Component | glyphosine (wt %) | NMG (ppm) | glyphosine partitioning (%) | NMG partitioning (%) |
|---|---|---|---|---|
| Run 9 ML | 0.33 | 3454 | — | — |
| Run 9 Wash | 0.20 | 1778 | 33.0 | 24.0 |
| Run 9 Dried Cake | 0.61 | 4069 | — | — |
| Run 10 ML | 0.33 | 3812 | — | — |
| Run 10 Wash | 0.20 | 1949 | 35.0 | 23.0 |
| Run 10 Dried Cake | 0.67 | 4152 | — | — |
| Ave. ML | 0.33 | 3633 | — | — |
| Ave. Wash | 0.20 | 1864 | 34.0 | 23.5 |
| Ave. Dried Cake | 0.64 | 4111 | — | — |

The glyphosine concentrations reported in this example are higher than other baseline examples but the glyphosine partitioning percentages did not significantly change. Moreover, NMG partitioning percentages were similar to those of other baseline examples.

Example 5

Another set of comparative PMIDA experiments, PM runs 14 and 19, were done without seeding to establish a baseline from which the effects of PMIDA seeding could be evaluated. The experiments were done using DSIDA1 and 37% formalin feed as the formaldehyde source. The formalin feed was not stepped down. Total feed times were 55 minutes for DSIDA1 and 60 minutes for formalin. Crystallizing event times for the two runs were different due to problems encountered in the run 14 formalin addition. Crystallization began after 50% formalin addition in run 14 and after 70% addition in run 19. The results are reported in Tables 5A and 5B below.

TABLE 5A

PMIDA profile of PM run 14 ML and slurry

| % formalin added | ML PMIDA (wt %) | Slurry PMIDA (wt %) |
|---|---|---|
| 39 | 17.1 | 14.9 |
| 46 | 18.7 | 16.8 |
| 52 | 20.2 | 18.2 |
| 60 | 21.3 | 19.6 |
| 68 | 13.9 | 21.0 |
| 74 | 10.4 | 22.0 |
| 96 | 7.0 | 23.6 |

TABLE 5B

| Component | glyphosine (wt %) | NMG (ppm) | glyphosine partitioning (%) | NMG partitioning (%) |
|---|---|---|---|---|
| Run 14 ML | 0.18 | 3719 | — | — |
| Run 14 Wash | 0.11 | 1669 | 36.3 | 28.1 |
| Run 14 Dried Cake | 0.44 | 6031 | — | — |
| Run 19 ML | 0.26 | 4215 | — | — |
| Run 19 Wash | 0.12 | 1809 | 33.6 | 25.4 |
| Run 19 Dried Cake | 0.45 | 4844 | — | — |
| Ave. ML | 0.21 | 3967 | — | — |
| Ave. Wash | 0.11 | 1739 | 34.9 | 26.7 |
| Ave. Dried Cake | 0.44 | 5438 | — | — |

The data of Table 5A indicate that the precipitation event in the absence of seed crystals behaves similarly to that of the other baseline experiments of examples 3 and 4 performed in the absence of seed crystals. The crystallization event occurred very rapidly with ML PMIDA concentrations dropping at rates of 0.7 to 1.5 wt % per minute. The data of Table 5B indicates that the mechanism of impurity incorporation was essentially the same as that of the other baseline experiments because while the actual wetcake impurities varied, the average partitioning percentages of glyphosine and NMG did not vary much between the experiments of examples 3, 4 and 5.

Example 6

In PM runs 4A to 4C a series of three DSIDA1-based PMIDA seeding experiments were done to evaluate the effect of late seeding; that is, seeding at a high degree of PMIDA supersaturation. The experiments were done using 43% formalin feed as the formaldehyde source and the formalin feed and addition of 2 to 2.5% of seed crystals, on a final batch weight basis, after about 50% of the formalin had been added to the reactor. Total feed times were between 50 and 60 minutes with the DSIDA1 and formalin feed rate being the same in each trial. The crystallization results are reported in Table 6A. ML, wash and wetcake samples were collected and analyzed with results reported in Table 6B.

TABLE 6A

Experimental conditions and results in late-seeding experiments.

| Run | DSIDA/formalin feed times (min) | Seed added (wt %) | % formalin added at seeding | % formalin added at crystal-lization |
|---|---|---|---|---|
| Run 4A | 60/60 | 2.0 | 48 | 70 |
| Run 4B | 50/50 | 2.0 | 50 | 60 |
| Run 4C | 55/55 | 2.6 | 45 | 55 |

TABLE 6B

Impurity results from late seeding experiments

| Component | glyphosine (wt %) | NMG (ppm) | glyphosine partitioning (%) | NMG partitioning (%) |
|---|---|---|---|---|
| Run 4A ML | 0.22 | 4121 | — | — |
| Run 4A Wash | 0.11 | 1954 | 32.6 | 29.7 |
| Run 4A Dried Cake | 0.35 | 5808 | — | — |
| Run 4B ML | 0.22 | 4445 | — | — |
| Run 4B Wash | 0.08 | 2629 | 34.5 | 24.6 |
| Run 4B Dried Cake | 0.40 | 5048 | — | — |
| Run 4C ML | 0.21 | 4102 | — | — |
| Run 4C Wash | 0.05 | 1980 | 36.6 | 29.5 |
| Run 4C Dried Cake | 0.40 | 5751 | — | — |
| Ave. ML | 0.22 | 4223 | — | — |
| Ave. Wash | 0.08 | 2188 | 34.6 | 27.9 |
| Ave. Dried Cake | 0.38 | 5536 | — | — |

The results indicate that late seeding appears to decrease glyphosine incorporation in the crystals as well as the partitioning coefficient as compared to baseline conditions.

In another series of seeding experiments, PM run 22 through 27, late seeding was done in the absence of either a feed stoppage or stepped feed. Those experiments evaluated the effect of various process parameters on impurity levels and impurity partitioning. In particular, in PM runs 22-24 DSIDA1 was used and the effect of glyphosine and NMG concentrations, both individually and in combination, on filtration performance of PMIDA slurries was examined. In PM runs 25-27 DSIDA2 was used to determine the effect of high levels of both glyphosine and NMG on filtration performance, as well as the impact of agitation rate on impurity partitioning and filtration performance.

The process conditions used for PM runs 22-27 were as follows. Each of runs 22-27 used 37% formalin. The runs varied primarily upon the spike type, agitation rate, and DSIDA feed used, while there were few differences between the seeding regimens. All experiments had feed times of 60 minutes and 65 minutes for DSIDA and formalin, respectively. PM run 22 used DSIDA1, contained a 0.51% NMG spike on a final batch weight basis, contained no glyphosine spike, and was agitated at 250 rpm. Seeding started at 30 minutes (at 46% of total formalin added), and 4.1% of seed on a final batch weight basis was added over 4 minutes (completed at 52% of total formalin added). PM run 23 used DSIDA1, contained no NMG or glyphosine spike, and was agitated at 250 rpm. Seeding started at 30 minutes (at 44% of total formalin added), and 4.1% of seed on a final batch weight basis was added over 4 minutes (completed at 50% of total formalin added). PM run 24 used DSIDA1, contained no NMG spike, contained a 0.2% spike of glyphosine on a final batch weight basis, and was agitated at 250 rpm. Seeding started at 32 minutes (at 46% of total formalin added), and 4.1% of seed on a final batch weight basis was added over 4 minutes (completed at 52% of total formalin added). PM run 25 used DSIDA2, contained no NMG or glyphosine spike, and was agitated at 250 rpm. Seeding started at 30 minutes (at 47% of total formalin added), and 4.1% of seed on a final batch weight basis was added over 4 minutes (completed at 54% of total formalin added). PM run 26 used DSIDA2, contained no NMG or glyphosine spike, and was agitated at 250 rpm. Seeding started at 30 minutes (at 49% of total formalin added), and 4.1% of seed on a final batch weight basis was added over 4 minutes (completed at 55% of total formalin added). PM run 27 used DSIDA2, contained no NMG or glyphosine spike, and was agitated at 500 rpm. Seeding started at 30 minutes (at 48% of total formalin added), and 4.1% of seed on a final batch weight basis was added over 4 minutes (completed at 54% of total formalin added).

Table 6C lists the impurity concentrations in the final components of PM runs 22-27. NMG data were not available for PM runs 23 and 24. No NMG was spiked for those runs and because DSIDA1 was used only trace amounts of NMG were present in the ML and wash samples.

TABLE 6C

Final component impurity analyses of late seeding experiments

| Component | glyphosine (wt %) | NMG (ppm) | glyphosine partitioning (%) | NMG partitioning (%) |
|---|---|---|---|---|
| Run 22 ML | 0.30 | 4900 | — | — |
| Run 22 Wash | 0.16 | 2527 | 33.1 | 25.9 |
| Run 22 Dried Cake | 0.50 | 5709 | — | — |
| Run 23 ML | 0.28 | N/A | — | — |
| Run 23 Wash | 0.14 | N/A | 34.5 | N/A |
| Run 23 Dried Cake | 0.49 | N/A | — | — |
| Run 24 ML | 0.55 | N/A | — | — |
| Run 24 Wash | 0.33 | N/A | 31.7 | N/A |
| Run 24 Dried Cake | 0.87 | N/A | — | — |
| Run 25 ML | 0.48 | 3730 | — | — |
| Run 25 Wash | 0.27 | 1949 | 29.8 | 24.3 |
| Run 25 Dried Cake | 0.70 | 4083 | — | — |
| Run 26 ML | 0.47 | 3689 | — | — |
| Run 26 Wash | 0.22 | 1671 | 29.2 | 25.5 |
| Run 26 Dried Cake | 0.65 | 4238 | — | — |
| Run 27 ML | 0.86 | 3424 | — | — |
| Run 27 Wash | 0.57 | 2169 | 18.6 | 17.0 |
| Run 27 Dried Cake | 0.84 | 2991 | — | — |

The data of Table 6C indicate that NMG does not appear to significantly influence glyphosine partitioning, as noted by the similar glyphosine partitioning percentages observed in runs 22 and 23. The late seeding strategy appeared effective in reducing the glyphosine partitioning percentages when DSIDA2 was used in PMIDA preparation.

Increased agitation was shown to reduce impurity incorporation. PM runs 25 and 26 were performed at an agitation rate of 250 rpm giving an average glyphosine partitioning of about 29.5% and an average wetcake NMG concentration of about 4160 ppm. PM run 27 was performed at 500 rpm. Even though much more glyphosine was produced in run 27 because DSIDA2 was used, glyphosine partitioning was reduced by about 36.5%. Reductions in run 27 wetcake NMG concentration are biased because the DSIDA2 sarcosine level was about 2780 ppm. The average sarcosine level of runs 25 and 26 was about 3430 ppm. Prior to adjusting for the lower sarcosine level, cake NMG concentration decreased by about 28.1%. If the amount of NMG produced is adjusted for a sarcosine level of about 3430 ppm, maintaining the same partitioning percentage, the cake NMG level is still reduced by about 18.0% to about 3413 ppm. It is believed, without being bound to any particular theory, that by increasing agitation rate, the boundary layer surrounding the PMIDA crystal is reduced, which in turn reduces the effective impurity-partitioning coefficient, as defined by equation 1.3.

Example 7

A series of eight seeding experiments were done to evaluate the effect of early seeding, or seeding at a relatively low to moderate degree of PMIDA supersaturation. In each run the seed was added over period of time in order to simulate commercial conditions where seed addition typically would occur linearly over a period of time (on the order of minutes), as opposed to a single, pulsed, addition typical of a laboratory or small scale trial.

DSIDA1 was used in PMIDA prepared in each of PM runs 5, 6A, 6B, 7 and 8.

In the first experiment, PM run 5, about 0.55% of NMG on a final batch weight basis was spiked into the PM reactor. About 1.3% grams of PMIDA seed on a final batch weight basis was added to the reactor after about 34% of the formalin had been added and another about 1.3% were added after 44% of the formalin was added. The concentration of the formalin feed was about 43%. The total seed added was about 2.6 wt % based on the final batch weight. The feeds were then stopped for about 10 minutes. The crystallization event was observed to occur over about 20 minutes, which was much more slowly than in non-seeded systems. Table 7A lists the impurity concentrations in the final components of run 5, as well at the impurity partitioning percentages. The high glyphosine values in run 5 were observed to result from high glycine content, about 2877 ppm, in the DSIDA feed used for that experiment.

TABLE 7A

PM run 5 final component impurity analyses

| Component | glyphosine (wt %) | NMG (ppm) | glyphosine partitioning (%) | NMG partitioning (%) |
|---|---|---|---|---|
| Run 5 ML | 0.33 | 4767 | — | — |
| Run 5 Wash | 0.19 | 2279 | 26.9 | 19.9 |
| Run 5 Dried Cake | 0.44 | 4235 | — | — |

In the second experiment, PM run 6A, about 0.55% of NMG on a final batch weight basis were spiked into the PM reactor, and the concentration of formalin in the feed was about 43%. About 1.0% of PMIDA seed on a final batch weight basis was added to the reactor after about 36% of the formalin had been added. Additional 1.0% seed additions were done every minute until about 44% of the formalin was added. The total seed added was about 4.0% based on the final batch weight. The feeds were then stopped for about 10 minutes. The crystallization event was observed almost immediately after feed stoppage. Table 7B lists the impurity concentrations in the final components of run 6A, as well at the impurity partitioning percentages. The data indicates that the glyphosine partitioning percentage was reduced.

TABLE 7B

PM run 6A final component impurity analyses

| Component | glyphosine (wt %) | NMG (ppm) | glyphosine partitioning (%) | NMG partitioning (%) |
|---|---|---|---|---|
| Run 6A ML | 0.27 | 3237 | — | — |
| Run 6A Wash | 0.16 | 1901 | 30.0 | 28.0 |
| Run 6A Dried Cake | 0.42 | 4674 | — | — |

In the third experiment, PM run 6B, about 0.55% of NMG on a final batch weight basis were spiked into the PM reactor, and the concentration of the formalin feed was about 43%. About 1.0% of PMIDA seed on a final batch weight basis was added to the reactor after about 34% of the formalin had been added. Additional 1.0% seed additions were done every minute until about 42% of the formalin was added. The total seed added was about 4.0 wt % based on the final batch weight. After seed addition was complete the feeds were then stopped for about 18 minutes. Table 7C lists the impurity concentrations in the final components of run 6B, as well at the impurity partitioning percentages.

TABLE 7C

PM run 6B final component impurity analyses

| Component | glyphosine (wt %) | NMG (ppm) | glyphosine partitioning (%) | NMG partitioning (%) |
|---|---|---|---|---|
| Run 6B ML | 0.33 | 4078 | — | — |
| Run 6B Wash | 0.17 | 1956 | 27.6 | 25.1 |
| Run 6B Dried Cake | 0.41 | 4466 | — | — |

In the fourth experiment, PM run 7, about 0.55% of NMG on a final batch weight basis were spiked into the PM reactor, and the concentration of the formalin feed was about 43%. About 1.0% of PMIDA seed on a final batch weight basis was added to the reactor after about 30% of the formalin had been added. Additional 1.0% seed additions were done every minute until about 38% of the formalin was added. The total seed added at that point was about 2.5 wt % based on the final batch weight. The feeds were then stopped for approximately 10 minutes, after which time another 1.6% of seed was added. The total feed stoppage was about 20 minutes. The crystallization crash event was observed to occur very slowly after the second seed addition. Table 7D lists the impurity concentrations in the final components of run 7, as well at the impurity partitioning percentages.

TABLE 7D

PM run 7 final component impurity analyses

| Component | glyphosine (wt %) | NMG (ppm) | Glyphosine partitioning (%) | NMG partitioning (%) |
|---|---|---|---|---|
| Run 7 ML | 0.34 | 4488 | — | — |
| Run 7 Wash | 0.13 | 2105 | 26.5 | 23.0 |
| Run 7 Dried Cake | 0.39 | 4342 | — | — |

In the fifth experiment, PM run 8, the PM reactor was spiked with about 0.55% of NMG on a final batch weight basis. Seeding began after about 35% formalin addition, and a total of about 4% seed, based on the final batch weight, was added over a 3 minute period at which point about 40% of the formalin had been added. The concentration of the formalin feed was about 43%. The formalin was added over 66 minutes and the DSIDA was added over about 60 minutes. Crystallization occurred gradually following the seed addition. The feed was not stopped in this experiment. Table 7E lists the impurity concentrations in the final components of run 8, as well at the impurity partitioning percentages.

TABLE 7E

PM run 8 final component impurity analyses

| Component | glyphosine (wt %) | NMG (ppm) | glyphosine partitioning (%) | NMG partitioning (%) |
|---|---|---|---|---|
| Run 8 ML | 0.23 | 3617 | — | — |
| Run 8 Wash | 0.11 | 1665 | 32.0 | 24.0 |
| Run 8 Dried Cake | 0.38 | 4140 | — | — |

In each of the PM runs 5, 6A, 6B, 7 and 8 of example 7, it is believed that glyphosine was present in the system due to conversion of glycine in the PM step. The glycine concentration in the DSIDA feed of each of those runs was about 2877 ppm glycine. A comparison of those five early seeding runs indicates that early seeding coupled with a feed stoppage proved most effective in reducing the amount of glyphosine that partitioned to the solid phase. The average glyphosine partitioning percentage for those runs was about 28.8%, and the average NMG concentration in the dried cake was 4404. Although all of the experiments had about equivalent reductions in dried cake NMG concentration, stepping down the formalin feed was not as effective in reducing glyphosine partitioning as stopping both feeds. This suggests that glyphosine partitioning is dependent upon both the crystallization event, as well as the rate at which it is produced.

Two more early seeding runs, PM run 12 and PM run 17, were done to evaluate a DSIDA2-based PMIDA feed source containing sarcosine as a contaminant. In those experiments, NMG was produced because of the sarcosine contaminant so NMG spikes were not added.

In PM run 12, seeding began after about 36% of the formalin had been added to the PM reactor with about 4.1% of seed, on a final batch weight basis, being added over about 4 minutes, after which the formalin feed was stepped down by about 33%. The concentration of the formalin feed was about 43%. About 46.5% of the available formalin had been added to the reactor when the formalin feed was stepped down. The crystallization event was observed to be very gradual, with light transmission slowly decreasing after the seed addition. Total feed times for PM run 12 were 60 and 65 minutes for DSIDA2 and formalin, respectively. Tables 7F and G show the ML and slurry compositions during the PM step for PM run 12.

TABLE 7F

PM run 12 ML composition profile

| % formalin added | PMIDA (wt %) | NMG (ppm) | glyphosine wt % |
|---|---|---|---|
| 27 | 12.9 | 3474 | 0.16 |
| 53 | 19.8 | 4252 | 0.31 |
| 68 | 16.9 | 4548 | 0.38 |
| 87 | 11.6 | 4589 | 0.45 |
| 100 | 7.6 | 4685 | 0.46 |

TABLE 7G

PM run 12 slurry composition profile

| % formalin added | PMIDA (wt %) | NMG (ppm) | Glyphosine wt % |
|---|---|---|---|
| 27 | 10.2 | 3070 | 0.12 |
| 53 | 18.9 | 3312 | 0.26 |
| 68 | 21.7 | 3704 | 0.36 |
| 87 | 23.2 | 3932 | 0.39 |
| 100 | 24.2 | 3952 | 0.44 |

PM run 12 indicates that early seeding slows down the crystallization rate, as shown by the decrease in the supersaturation shedding rate. A comparison of between PM run 12 and PM run 11 (a baseline experiment run without seeding; see Example 3 at Tables 3E and 3F) shows that the crystallization event occurs later in the baseline case and ML PMIDA supersaturation is shed at a much higher rate and crashes from solution. In PM run 11 the ML PMIDA concentration dropped from about 23.7% to about 13.1 wt % in about 10 minutes, resulting in a shedding rate of 1.1 wt % per minute. In PM run 12, the PMIDA shedding rate did not exceed about 0.4 wt % per minute. That result was qualitatively confirmed as the loss of light transmission rate in PM run 12 was much more gradual than in the case of the non-seeded experiments.

In PM run 17, seeding began after about 31% of the formalin had been added to the PM reactor with about 4.1% grams on final batch weight basis being added over about 4 minutes, after which the formalin feed was stepped down by about 33%. About 40.0% of the available formalin had been added to the reactor when the formalin feed was stepped down. The concentration of the formalin feed was about 43%. The crystallization event was observed to be very gradual, with light transmission slowly decreasing after the seed addition. Total feed times for PM run 17 were 60 and 65 minutes for DSIDA2 and formalin, respectively. Table 7H compares the impurity concentrations in the final components of PM runs 12 and 17 as well as their respective impurity partitioning.

TABLE 7H

Final component impurity analyses from PM run 12 and PM run 17

| Component | glyphosine (wt %) | NMG (ppm) | glyphosine partitioning (%) | NMG partitioning (%) |
|---|---|---|---|---|
| Run 12 ML | 0.40 | 3720 | — | — |
| Run 12 Wash | 0.22 | 1941 | 29.1 | 20.9 |
| Run 12 Dried Cake | 0.60 | 3592 | — | — |
| Run 17 ML | 0.39 | 3822 | — | — |
| Run 17 Wash | 0.18 | 1829 | 30.6 | 22.7 |
| Run 17 Dried Cake | 0.59 | 3872 | — | — |
| Ave. ML | 0.39 | 3771 | — | — |
| Ave. Wash | 0.20 | 1885 | 29.1 | 21.8 |
| Ave. Dried Cake | 0.59 | 3726 | — | — |

The results of Table 7H indicate that early seeding coupled with formalin feed stepping decrease glyphosine partitioning and NMG dried cake concentration. In comparison to unseeded PM runs 9 and 10 (see Table 5D), the average glyphosine partitioning percentage decreased by a little more than about 12%, from 34.0% to 29.1%, while there was about a 9% reduction in the cake NMG concentration, from about 4111 to about 3726. These results indicate that early seeding coupled with stepped formalin feed can reduce impurity partitioning.

Example 8

In PM run 18, an experiment was done to determine the effect of seeding at an intermediate level of supersaturation on DSIDA2-based PMIDA. Previous work (PM runs 4A to 4C of Example 6) indicated that seeding closer to the crystallization event gave wetcakes having improved filtration performance. That data showed that seeding after approximately 50% of the available formalin had been added provided no significant reduction in impurity partitioning. This experiment evaluated seeding after about 40% to about 45% of the formalin had been added to the reactor. After about 43% of the formalin had been added to the PM reactor, about 4.1% of seed on a final batch weight basis were added over about 4 minutes. After about 51% of the formalin was added, its feed rate was stepped down by about 33%. Total feed times of 60 minutes and 65 minutes for DSIDA2 and formalin, respectively, were used. The crystallization event occurred shortly after the seed crystals were added. The impurity concentrations in the final components and the impurity partitioning percentages of PM run 18 are given in Table 8A.

TABLE 8A

PM run 18 final component impurity analyses

| Component | glyphosine (wt %) | NMG (ppm) | glyphosine partitioning (%) | NMG partitioning (%) |
|---|---|---|---|---|
| Run 18 ML | 0.44 | 3668 | — | — |
| Run 18 Wash | 0.22 | 1826 | 26.1 | 22.8 |
| Run 18 Dried Cake | 0.53 | 3726 | — | — |

A comparison of the results of PM run 18 to the averages of the baseline (PM runs 9 and 10, Table 5D) and early seeding experiments (PM runs 12 and 17, Table 8J) indicates that intermediate seeding also is effective in reducing impurity concentrations and partitioning percentages. The average data for PM runs 9 & 10 and PM runs 12 & 17 is summarized below in Table 8B.

TABLE 8B

| Component | glyphosine (wt %) | NMG (ppm) | glyphosine partitioning (%) | NMG partitioning (%) |
|---|---|---|---|---|
| Run 9/10 ML average | 0.33 | 3633 | — | — |
| Run 9/10 Wash average | 0.20 | 1864 | 34.0 | 23.5 |
| Run 9/10 Dried Cake average | 0.64 | 4111 | — | — |
| Run 12/17 ML average | 0.39 | 3771 | — | — |
| Run 12/17 Wash average | 0.20 | 1885 | 29.1 | 21.8 |
| Run 12/17 Dried Cake average | 0.59 | 3726 | — | — |

A comparison of the data of Tables 8A and 8B indicates that both early and intermediate seeding reduced NMG concentration in the solid phase by about 9.4%. The data shows that intermediate seeding appears to reduce the glyphosine partitioning percentage more then the early seeding, but that may be due to more effective cake washing.

PM run 15 evaluated the effectiveness of seeding at an intermediate time on reducing impurity partitioning. In this run DSIDA1 was used and seeding began after about 43% of the formalin had been added. About 0.55% of NMG on a final batch weight basis were charged to the PM reactor. The concentration of the formalin used in this run was about 37%. About 4.1% of seed on a final batch weight basis were added over about 4 minutes, after which the formalin feed rate was stepped down by about 33%. About 51% of the available formalin had been added to the PM reactor when the feed rate was stepped down. The crystallization event was observed to occur gradually after the seed addition. Total feed times were about 63 minutes and about 68 minutes for DSIDA and formalin, respectively. Table 8C gives the impurity concentrations in the final components of the run, as well as the impurity partitioning percentages.

TABLE 8C

PM run 15 final component impurity analyses

| Component | glyphosine (wt %) | NMG (ppm) | glyphosine partitioning (%) | NMG partitioning (%) |
|---|---|---|---|---|
| Run 15 ML | 0.22 | 3945 | — | — |
| Run 15 Wash | 0.10 | 2050 | 34.2 | 22.4 |
| Run 15 Dried Cake | 0.43 | 4286 | — | — |

The NMG concentration of the dried cake closely resembled the results from other seeded runs, suggesting that the strategy of run 15 was effective in reducing impurity concentrations. A reduction in the glyphosine partitioning percentage was not observed, due in part to an ineffective cake wash. The average glyphosine concentration of the washes was about 0.19 wt %, but it was almost 50% lower in run 15. Given this change in wash glyphosine concentration, it cannot be concluded that the seeding strategy was ineffective in reducing glyphosine partitioning. The seeding strategy of PM run 15 was effective in reducing cake NMG concentration and that strategy resulted in reduced amounts of impurity incorporation.

Example 9

Several laboratory experiments using an interrupted feed were performed to evaluate supersaturation limits during seeding and the initial stages of the crystallization event. The PM feed amounts were altered such that only a portion of the typical feed amounts were used in order to simulate various stages of the PM reaction step. The first two experiments were designed such that only about 40% of the typical feed amounts were used in order to mimic reactor conditions that occurred during seed addition of early-seeding experiments. These experiments utilized a 60:40 DSIDA split between the hydrolyzer and PM reactor, 43% formalin, and DSIDA1. In the first experiment, a spike of about 0.3% of NMG on a final batch weight basis was added to the reactor following the hydrolysis step. Following the PM reaction, about 6.4% of seed on a final batch weight basis were added after the feeds were completed and a sample was removed. Post-seed samples were removed at 20, 40 and 100 minutes following the seed addition to determine the rate at which supersaturation would be relieved. All of the samples were taken at approximately 105° C. As the temperature decreased, additional samples were taken at 75° C. and 50° C. The first experiment data are in Table 9A below.

TABLE 9A

ML sample data from PM interrupted run 1

| ML sample ID | PMIDA (wt %) |
|---|---|
| 5 minutes after feed completion | 16.2 |
| 20 minutes after seed addition | 15.5 |
| 40 minutes after seed addition | 14.6 |
| 100 minutes after seed addition | 13.7 |
| Equilibrium at 105° C. | 12.4 |
| Equilibrium at 75° C. | 5.3 |
| Equilibrium at 50° C. | 3.3 |

In the second experiment, no NMG was added after the hydrolysis step, and seed crystals were not added. Post-feed samples were removed at 0, 60 and 240 minutes following completion of the feed addition. The second experiment data are in Table 9B below.

TABLE 9B

ML sample data from PM interrupted run 2

| ML sample ID | PMIDA (wt %) |
|---|---|
| 0 minutes after feed completion | 21.0 |
| 60 minutes after feed completion | 15.6 |
| 240 minutes after feed completion | 14.0 |
| Equilibrium at 105° C. | 13.8 |
| Equilibrium at 75° C. | 8.1 |
| Equilibrium at 50° C. | 4.0 |

The data in Table 9B indicate that low levels of supersaturation will relieve over time. Seeding accelerates that process, as seen in Table 9A, by supplying nuclei for crystal growth. Solubility experiments indicate that the PMIDA solubility limit in acidified ML at 105° C. is between about 6.4 wt % and about 8.5 wt %. As noted in Tables 9A and 9B, equilibrium samples were also taken at various temperatures. Averaging the data, the PM mother liquor was found to have a PMIDA concentration of about 16.4 wt % at 105° C.

A third experiment was designed such that only about 70% of the typical feed amounts were used in order to simulate PM reactor conditions when the PMIDA crystallization event typically takes place. The experiment utilized a 60:40 DSIDA split between the hydrolyzer and PM reactor, 37% formalin, and DSIDA1. No NMG was added after the hydrolysis step, and seed crystals were not added. Following the completion of the feeds, the reactor contents were allowed to mix at 105° C. for approximately 21 hours before sampling. At 105° C., the equilibrium mother liquor PMIDA concentration was found to be 8.6 wt %.

The fourth experiment was designed such that 100% of the typical feed amounts were added to the reactor in order to determine the equilibrium PMIDA solubility of the mother liquor after all of the feeds had been added. This experiment utilized a 60:40 DSIDA split between the hydrolyzer and PM reactor, 37% formalin, and DSIDA1. No NMG was added after the hydrolysis step, and seed crystals were not added. Following completion of the feeds, the reactor contents were allowed to mix at 105° C. for approximately 21 hours before sampling. At 105° C., the equilibrium mother liquor PMIDA concentration was found to be 5.9 wt %. This suggests that the mother liquor PMIDA solubility limit changes over the course of the PM reaction. Thus, it is believed, without being bound to any particular theory, that as the PM reaction progresses, supersaturation increase is a function of both PMIDA in situ generation and a decreasing solubility limit.

A fifth experiment was designed to determine the equilibrium mother liquor PMIDA concentration just prior to the crystallization event when a 75:25 DSIDA feed split is used. In addition to the feed split, the experiment used 37% formalin and DSIDA1. No NMG was added after the hydrolysis step, and seed crystals were not added. Mother liquor samples were removed during the course of the experiment. After about 84% of the total formalin had been added, the crystallization event began and the feeds to the reactor were stopped. The contents were allowed to mix at 105° C. for approximately 19 hours before sampling. Data is provided in Table 8C below.

TABLE 9C

ML sample data from PM interrupted run 5

| ML sample ID | % of total formalin added to PM reactor | PMIDA (wt %) |
|---|---|---|
| ML sample 1 | 19.7% | 7.8 |
| ML sample 2 | 34.2% | 13.8 |
| ML sample 3 | 48.4% | 18.4 |
| ML sample 4 | 63.3% | 22.1 |
| ML sample 5 | 77.2% | 24.0 |
| Equilibrium at 105° C. | 84.0% | 14.4 |

Example 10

Experiments were done to evaluate the effect of process parameters on the filtration performance of PMIDA wetcake. The factors include, without limitation, seeding amounts, seeding times, feed rates, agitation and impurity concentrations.

From the test data of PM runs 15-26, slurry and filtrate specific gravity were calculated, along with the percentage of solids found in the slurry and a modified filtration rate. The data were entered into a FDFit 2.0 program available from Aspen Technology Inc. The FDFit 2.0 software was used to fit a curve to the filtrate volume versus time data. Using the program several cake properties including cake porosity, porosity for a saturated cake, cake saturation, and cake permeability for PM runs 15-26 were calculated. The results are presented in Table 10A. In that table: "run" represents the PM run number; "calc. perm." represents calculated permeability in $cm^2$; "filt. rate" represents modified filtration rate in mL·cm/min; "ave. size" represents average median chord size; "ave. count" represents average total counts/second; and "solids" represents total wt % solids in the slurry. As to "seed time," "early" represents seeding at a relatively low a value of between about 1.2 and about 1.5, "inter." represents seeding at an intermediate a value of between about 1.5 and about 1.8, and "late" represents seeding at a relatively high σ value of between about 1.8 and about 2.0.

TABLE 10A

| Run | Seed Time | Calc. Perm | Filt. Rate | Ave. Size | Ave. Count | Solids |
|---|---|---|---|---|---|---|
| 15 | inter.[a] | $7.54 \times 10^{-9}$ | 183.2 | 7.31 | 21025 | 21.6 |
| 16 | no seed | $9.54 \times 10^{-9}$ | 182.7 | 7.12 | 25363 | 27.7 |
| 17 | Early | $9.56 \times 10^{-9}$ | 192.5 | 7.11 | 22884 | 23.1 |
| 18 | inter. | $1.12 \times 10^{-8}$ | 223.6 | 7.51 | 22413 | 23.4 |
| 19 | no seed | $8.56 \times 10^{-9}$ | 176.7 | 7.51 | 21708 | 23.0 |
| 20 | Early | $5.74 \times 10^{-9}$ | 129.3 | 7.17 | 23766 | 20.4 |
| 21 | Early | $7.68 \times 10^{-9}$ | 164.5 | 6.82 | 23648 | 23.0 |
| 22 | late[a] | $6.17 \times 10^{-9}$ | 138.0 | 7.05 | 21701 | 23.9 |
| 23 | Late | $9.76 \times 10^{-9}$ | 205.0 | 7.18 | 22710 | 23.7 |
| 24 | late[a] | $6.77 \times 10^{-9}$ | 154.1 | 7.23 | 23306 | 23.5 |
| 25 | late[a] | $3.71 \times 10^{-9}$ | 82.6 | 7.00 | 22386 | 23.5 |
| 26 | late[a] | $4.81 \times 10^{-9}$ | 106.6 | 6.96 | 23476 | 23.6 |

[a] added impurities

The two runs with the highest permeability and modified filtration rate are PM runs 18 and 23. PM run 18 was an intermediate seeding run with PMIDA prepared from DSIDA2. PM run 23 was a late seeding run with PMIDA prepared from DSIDA1 with no added impurities. PM runs 22 and 24-26 contained added impurities resulting in biased permeability and filtration rate calculations. PM run 19 was a baseline experiment in which no seeding was done in preparation of PMIDA from DSIDA2. PM run 16 can be considered a baseline experiment for PMIDA prepared from DSIDA1. The filtration rate and permeability for PM runs 19 and 16 are comparable. In both runs 19 and 16, the permeability and filtration rates are at least about 15% lower than those found in PM runs 18 and 23. Seeding close to the crystallization event appears to increase filtration performance. From Table 10A, it therefore appears that late seeding experiments have increased filtration performance as compared to early seeding experiments. The average modified filtration rate of the early seeding experiments not having added impurities was about 162.1 mL·cm/min. The average modified filtration rate of the intermediate and late seeding experiments not having added impurities was about 214.3 mL·cm/min, which is about 32% higher than the early seeding average.

PM runs 22 to 26 were all late seeding experiments that varied in added impurity concentration, with run 23 containing no added impurity. For those runs, slurry impurity concentrations were calculated from the weights of recovered ML and wetcake, and the impurity concentration found in each of them. The data are reported in Table 10B. In Table 10B: [glyphosine] is the slurry glyphosine concentration in wt %; [NMG] is the slurry NMG concentration in ppm; [impurity] is the sum of the glyphosine and NMG impurity concentrations in ppm; and the modified filtration rate is reported in mL·cm/min.

TABLE 10B

Impurity and filtration data from PM runs 22 through 26.

| PM Run | [glyphosine] | [NMG] | [impurity] | filtration rate |
|---|---|---|---|---|
| 22 | 0.361 | 5259 | 8868 | 138.0 |
| 23 | 0.334 | 300 | 3640 | 205.0 |
| 24 | 0.646 | 321 | 6780 | 154.1 |
| 25 | 0.554 | 3949 | 9490 | 82.6 |
| 26 | 0.527 | 3928 | 8202 | 106.6 |

The data for Table 10B are depicted in FIG. 4 which is a plot of the total slurry impurity concentration versus the filtration rate. The dashed lines are the 95% confidence limits for the trend fit line. The dotted lines are the 95% confidence limits for the individual data points. FIG. 4 shows that as the overall impurity concentration in the slurry increases, the modified filtration rate decreases.

Example 11

Experiments were done to evaluate the effect seeding reaction systems where about 60% of the DSIDA is feed is added to the hydrolyzer and the remainder of the DSIDA is fed to phosphonomethylation reactor. In particular, the experiments evaluated the effect of seed quantity and addition time on formed cake permeability. Experimental conditions include use of a 44% formalin feed solution, a linear formalin feed rate, and a total formalin feed time of 55 minutes. Primary nucleation is estimated to occur at about 70% formaldehyde charge in the absence of seed. The data are reported in Tables 11A and 11B below wherein in each experiment the seed quantity is based on the percent weight of the final product, the seed add time is reported in minutes after the start of the phosphonomethylation reaction, total seed addition time was about 6 minutes, cake permeability is reported in $cm^2$, and crystal size is the average median chord size in micrometers. Values for σ were estimated based on the amount of the formaldehyde source charged to the phosphonomethylation reactor.

TABLE 11A

| Run | Seed Start Time (min) | % Formalin Added at Seed Start | σ (estimated) | Seed Quantity | Cake Perm. | Crystal Size |
|---|---|---|---|---|---|---|
| 4 | no seed | N/A | — | no seed | $1.56 \times 10^{-8}$ | 8.46 |
| 5 | 35 | 64% | 1.9 | 1.0% | $1.77 \times 10^{-8}$ | 7.83 |
| 7 | 35 | 64% | 1.9 | 2.0% | $2.40 \times 10^{-8}$ | 7.86 |
| 8 | 30 | 55% | 1.7 | 2.0% | $2.46 \times 10^{-8}$ | 8.03 |
| 9 | 27 | 49% | 1.5 | 1.0% | $2.74 \times 10^{-8}$ | 8.27 |
| 10 | 20 | 36% | 1.1 | 1.0% | $1.82 \times 10^{-8}$ | — |
| 11 | 30 | 55% | 1.7 | 0.5% | $1.79 \times 10^{-8}$ | — |
| 12 | 25 | 45% | 1.4 | 1.0% | $1.94 \times 10^{-8}$ | — |
| 13 | 23 | 42% | 1.3 | 1.0% | $1.76 \times 10^{-8}$ | — |

The data indicate that seeding generally increases cake permeability with the average permeability increasing to about $2.09 \times 10^{-8}$ $cm^2$, a permeability increase of about 34%. The data also indicate that at least about 0.5%, on a final batch weight basis, seed enhances cake permeability. The data further indicate that the optimum seeding time for maximizing cake permeability is at a σ value of about 1.5 to about 1.9 with a seed amount of at least about 1% by weight. However, increased cake permeability over that observed for unseeded systems was found when seeding at 0.5 wt % or at σ as low as about 1.1.

The data further show that although seeding increases cake permeability, seeding also appeared to give a reduced average crystal median chord length. Further analysis of the particle size distribution suggests that while the median chord length decreased with seeding, the number particles having a size of less than one micro meter decreased with seeding.

The data further indicate that cake permeability increases as the point of seeding approaches the point of spontaneous nucleation. Stated another way, when seeding within the supersaturated zone, cake porosity increases as the degree of supersaturation increases.

Commercial scale experiments were done to evaluate the effect of σ, total seed addition time, and seed quantity on PMIDA wetcake permeability (reported in $cm^2$), moisture (g moisture/g wetcake) and porosity. The results are reported in Table 11B.

TABLE 11B

| Seeding Conditions | σ (estimated) | # of runs | Cake Perm. | Moisture | Porosity |
|---|---|---|---|---|---|
| No seed | — | 7 | $1.38 \times 10^{-8}$ | 0.30 | 0.52 |
| 2% seed at 35 min | 1.8 | 6 | $1.88 \times 10^{-8}$ | 0.30 | 0.57 |
| 4% seed at 35 min | 1.8 | 1 | $1.14 \times 10^{-8}$ | 0.39 | 0.56 |
| 2% seed at 40 min | 2.0 | 2 | $1.74 \times 10^{-8}$ | 0.30 | 0.56 |
| 2% seed at 40 min $^a$ | 2.0 | 1 | $1.00 \times 10^{-8}$ | 0.39 | 0.50 |
| 2% seed at 45 min | 2.1 | 2 | $1.33 \times 10^{-8}$ | 0.34 | 0.54 |

$^a$ Seed added over 3 minutes; seed addition time for all other runs was 6 minutes.

The data indicate that batches seeded with 2 wt % seed at 35 minutes (σ estimated to be about 1.8) produced wetcake having about 36% higher permeability and about 10% higher porosity than unseeded batches, and batches seeded with 2 wt % seed at 40 minutes (σ estimated to be about 2.0) produced wetcake having about 26% higher permeability and about 8% higher porosity than unseeded batches.

Example 12

Experiments were done to evaluate the effect of seeding reaction systems where about 75% of the DSIDA is feed is added to the hydrolyzer and the remainder of the DSIDA is fed to phosphonomethylation reactor. In particular, the experiments evaluated the effect of seed quantity and addition time on formed cake permeability. The data are reported in Table 12A below wherein in each experiment a 44% formalin feed solution was used, a formalin feed time of 55 minutes was used, the seed quantity is based on the percent weight of the final product, the seed add time is reported in minutes after the start of the phosphonomethylation reaction, total seed addition time was about 3 minutes, cake permeability is reported in $cm^2$, and crystal size is the average median chord size in micrometers. Values for σ were estimated based on the amount of the formaldehyde source charged to the phosphonomethylation reactor.

TABLE 12A

| Run | Seed Time (min) | σ (estimated) | Seed Quantity | Cake Perm. | Crystal Size |
|---|---|---|---|---|---|
| 14 | no seed | — | no seed | $1.77 \times 10^{-8}$ | 9.38 |
| 16 | no seed | — | no seed | $3.68 \times 10^{-8}$ | 9.15 |
| 17 | no seed | — | no seed | $2.40 \times 10^{-8}$ | 8.94 |
| 18 | 35 | 1.9 | 2% | $3.50 \times 10^{-8}$ | 10.14 |
| 19 | 33 | 1.8 | 2% | $3.35 \times 10^{-8}$ | 9.39 |

The data suggest that seeding is effective in increasing wetcake permeability and particle size at the 75%/25% split DSIDA feed rate. For unseeded runs the average median chord length and permeability were 9.16 and $2.62 \times 10^{-8}$, respectively, while for the seeded runs the averages were 9.76 and $3.43 \times 10^{-8}$, respectively. Thus seeding increased median chord length and permeability by 7% and 31%, respectively.

Example 13

Experiments were done to determine the effect of agitation speed on cake permeability. Reactor agitation speed was reduced from 100 rpm to 50 rpm for several batches each day for 3 days. Samples were collected from crystallizers and then analyzed for changes in particle size, permeability and chemistry. There were no significant differences observed in particle size and chemistry at the two speeds investigated. The results are reported in Table 13A below wherein the agitation speed is reported in rpm, cake permeability is reported in $cm^2$, cake moisture is based on a saturated cake and is reported in grams moisture per gram of cake, and cake porosity is reported as $cm^3$.

TABLE 13A

| Agitation speed | Cake permeability | Cake moisture | Cake porosity |
|---|---|---|---|
| 100 | $1.63 \times 10^{-8}$ | 0.31 | 0.50 |
| 50 | $1.97 \times 10^{-8}$ | 0.29 | 0.54 |

The data presented in Table 13A indicate filtration benefits by operating the PM reactor at a lower agitation speed. Average cake permeability increased by 20%, cake moisture decreased by 6%, and cake porosity increased by 7%. Moreover, data suggest that by operating at lower agitation speed, wetcake dewatering capabilities are enhanced.

Laboratory scale experiments were also performed to determine the effect of agitation speed on cake filtration performance. From the test data of PM runs 25-27, slurry and filtration specific gravity were calculated, along with the percentage of solids found in the slurry and a modified filtration rate. The data were entered into a FDFit 2.0 program available from Aspen Technology Inc. The FDFit 2.0 software was used to fit a curve to the filtrate volume versus time data. Using the program, several cake properties including cake porosity, porosity for a saturated cake, cake saturation, and cake permeability for PM runs 25-27 were calculated. The results are presented in Table 13B. In that table: "run" represents the PM run number; "calc. perm." represents calculated permeability in $cm^2$; "filt. rate" represents modified filtration rate in mL cm/min; "ave. size" represents average median chord size; "ave. count" represents average total counts/sec; and "solids" represents total wt % solids in the slurry.

TABLE 13B

| Run | Calc. perm | Filt. rate | Ave. size | Ave. count | solids |
|---|---|---|---|---|---|
| 25 | $3.71 \times 10^{-9}$ | 82.6 | 7.00 | 22836 | 23.5 |
| 26 | $4.81 \times 10^{-9}$ | 106.6 | 6.96 | 23476 | 23.6 |
| 27 | N/A | 3.8 | 6.73 | 26666 | 19.9 |

Data in Table 13B indicates that increasing the agitation rate from 250 rpm to 500 rpm resulted in a decrease in the average particle size as well as a decrease in filtration rate. It is believed, without being bound to any particular theory, that the higher agitation rate increased shear force on the growing crystals thereby pulling off weaker parts of the crystal. Moreover, the higher agitation rate could also increase the likelihood of impeller collisions that may fracture some of the crystals in a process termed attrition, thereby creating smaller crystals and a larger proportion of fines.

Example 14

The glyphosine and NMG partitioning coefficients for experimental PM runs 1-3, 9-11 and 14 (no seeding), 5-8, 12,17 and 20 (early seeding), 15 and 18 (intermediate seeding) and 4, 19, 21-26 (late seeding) were calculated in order to determine the effect of seeding time on glyphosine and NMG partitioning to the PMIDA dried PMIDA filter cake. The partitioning coefficient was calculated by dividing the dried filter cake impurity (glyphosine or NMG) concentration (wt %) by the corresponding mother liquor concentration. The results are reported in Table 14A below. The data from experimental PM runs 13 and 16 was not included because those runs had a significant amount of glyphosine added to the experiment thus biasing the glyphosine partitioning results. The data from experimental PM run 27 was not included because the agitation rate for that experiment was 500 rpm as compared to experimental runs 1-26 that utilized as 250 rpm agitation rate.

TABLE 14A

|  | filter cake:ML (glyphosine) | filter cake:ML (NMG) |
|---|---|---|
| Non-seeded PM runs |  |  |
| PM run 1 | 2.08:1 | 1.26:1 |
| PM run 2 | 1.42:1 | 1.10:1 |
| PM run 3 | 1.67:1 | not determined |
| PM run 3 (repeat) | 1.54:1 | not determined |
| PM run 9 | 1.83:1 | 1.18:1 |
| PM run 10 | 2.05:1 | 1.09:1 |
| PM run 11 | 2.02:1 | 1.15:1 |
| PM run 14 | 2.39:1 | 1.62:1 |
| Non-seeded averages | 1.88:1 | 1.23:1 |
| Early seeded PM runs |  |  |
| PM run 5 | 1.61:1 | 0.91:1 |
| PM run 6 | 1.59:1 | 1.44:1 |
| PM run 6 (repeat) | 1.25:1 | 1.10:1 |
| PM run 7 | 1.15:1 | 0.97:1 |
| PM run 8 | 1.68:1 | 1.14:1 |
| PM run 12 | 1.51:1 | 0.97:1 |
| PM run 17 | 1.52:1 | 1.01:1 |
| PM run 20 | 1.50:1 | 1.23:1 |
| Early seeding averages | 1.45:1 | 1.07:1 |
| Inter. seeded PM runs |  |  |
| PM run 15 | 1.96:1 | 1.09:1 |
| PM run 18 | 1.21:1 | 1.02:1 |
| Inter. seeding averages | 1.59:1 | 1.06:1 |
| Late seeded PM runs |  |  |
| PM run 4 | 1.59:1 | 1.41:1 |
| PM run 4 (first repeat) | 1.79:1 | 1.14:1 |
| PM run 4 (second repeat) | 1.90:1 | 1.40:1 |
| PM run 19 | 1.75:1 | 1.17:1 |
| PM run 21 | 1.50:1 | 1.10:1 |
| PM run 22 | 1.65:1 | 1.17:1 |
| PM run 23 | 1.76:1 | not determined |
| PM run 24 | 1.58:1 | not determined |
| PM run 25 | 1.45:1 | 1.10:1 |
| PM run 26 | 1.39:1 | 1.15:1 |
| Late seeding averages | 1.64:1 | 1.21:1 |
| Overall averages | 1.57:1 | 1.14:1 |

As indicated by the calculated partitioning coefficient, the results indicate that early seeding appears to be the most effective at reducing glyphosine partitioning to the filter cake. Intermediate seeding was less effective than early seeding, while late seeding was least effective. Seeding at any point in time reduced glyphosine partitioning to the filter cake as compared to non-seeded systems. Seeding also reduces NMG partitioning to the filter cake, but the efficiency is not as great as for glyphosine partitioning.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

When introducing elements of the present invention or the preferred embodiments thereof, the articles "a", "an", "the", and "said" are intended to mean that there are one or more of the elements. The terms "comprising", "including," and "having" are intended to be inclusive and mean that there may be additional elements other than the listed elements.

What is claimed is:

1. A process for preparing and crystallizing N-(phosphonomethyl)iminodiacetic acid, the process comprising:
combining an alkali metal salt of iminodiacetic acid, a strong mineral acid, a source of phosphorous acid and a source of formaldehyde to form a reaction solution comprising N-(phosphonomethyl)iminodiacetic acid;
adding N-(phosphonomethyl)iminodiacetic acid seed crystals to the reaction solution; and
inducing a degree of saturation in the reaction solution sufficient to cause crystallization of N-(phosphonomethyl)iminodiacetic acid onto the seed crystals, wherein inducing saturation comprises reacting components of the reaction solution to increase the concentration of N-(phosphonomethyl)iminodiacetic acid.

2. The process as set forth in claim 1 wherein a finished reaction solution is formed and the N-(phosphonomethyl)iminodiacetic acid seed crystals are charged to the reaction solution in a concentration of from about 0.5% to about 6% by weight of the total weight of N-(phosphonomethyl)iminodiacetic acid in the finished reaction solution on a dry basis.

3. The process as set forth in claim 1 wherein the reaction solution to which the N-(phosphonomethyl)iminodiacetic acid seed crystals are added has a supersaturated concentration of N-(phosphonomethyl)iminodiacetic acid between about $0\sigma$ and about $2\sigma$.

4. The process as set forth in claim 3 wherein the reaction solution to which the N-(phosphonomethyl)iminodiacetic acid seed crystals are added has a supersaturated concentration of N-(phosphonomethyl)iminodiacetic acid greater than about $1.5\sigma$.

5. The process as set forth in claim 4 wherein a bed comprising crystallized N-(phosphonomethyl)iminodiacetic acid is formed, the bed having a permeability greater than a bed of crystallized N-(phosphonomethyl)iminodiacetic acid prepared by an otherwise identical process in which no seed crystals are introduced.

6. The process as set forth in claim 4 wherein a bed comprising crystallized N-(phosphonomethyl)iminodiacetic acid is formed, the bed having a filtration rate greater than a bed of crystallized N-(phosphonomethyl)iminodiacetic acid prepared by an otherwise identical process in which no seed crystals are introduced.

7. The process as set forth in claim 4 wherein a bed comprising crystallized N-(phosphonomethyl)iminodiacetic acid is formed, the bed having a porosity greater than a bed of crystallized N-(phosphonomethyl)iminodiacetic acid prepared by an otherwise identical process in which no seed crystals are introduced.

8. The process as set forth in claim 4 wherein the yield of crystallized N-(phosphonomethyl)iminodiacetic acid is greater than the yield of crystallized N-(phosphonomethyl)iminodiacetic acid prepared by an otherwise identical process in which no seed crystals are introduced.

9. The process as set forth in claim 4 wherein a bed comprising crystallized N-(phosphonomethyl)iminodiacetic acid is formed, the bed having a lower total impurity concentration on a dry basis than a bed of crystallized N-(phosphonomethyl)iminodiacetic acid prepared by an otherwise identical process in which no seed crystals are introduced.

10. The process as set forth in claim 9 wherein the bed comprising crystallized N-(phosphonomethyl)iminodiacetic acid formed has a chloride content of less than about 5000 ppm by weight on a dry basis.

11. The process as set forth in claim 10 wherein the bed comprising crystallized N-(phosphonomethyl)iminodiacetic acid formed has a chloride content of less than about 3000 ppm by weight on a dry basis.

12. The process as set forth in claim 11 wherein the bed comprising crystallized N-(phosphonomethyl)iminodiacetic acid formed has a chloride content of less than about 1000 ppm by weight on a dry basis.

13. The process as set forth in claim 12 wherein the bed comprising crystallized N-(phosphonomethyl)iminodiacetic acid formed has a chloride content of less than about 250 ppm by weight on a dry basis.

14. The process as set forth in claim 9 wherein the bed comprising crystallized N-(phosphonomethyl)iminodiacetic acid formed has an N-methyl-N-(phosphonomethyl)glycine content of less than about 9,000 ppm by weight on a dry basis.

15. The process as set forth in claim 9 wherein the bed comprising crystallized N-(phosphonomethyl)iminodiacetic acid formed has an N,N-bis(phosphonomethyl)glycine content of less than about 10,000 ppm by weight on a dry basis.

16. The process as set forth in claim 4 wherein a bed comprising crystallized N-(phosphonomethyl)iminodiacetic acid is formed, the bed having a chloride content of less than about 1000 ppm by weight on a dry basis and a permeability of at least about $1 \times 10^{-9}$ cm$^2$.

17. The process as set forth in claim 3 wherein the reaction solution to which the N-(phosphonomethyl)iminodiacetic acid seed crystals are added has a supersaturated concentration of N-(phosphonomethyl)iminodiacetic acid less than about $0.5\sigma$.

18. The process as set forth in claim 17 wherein a bed comprising crystallized N-(phosphonomethyl)iminodiacetic acid is formed, the bed having a permeability greater than a bed of crystallized N-(phosphonomethyl)iminodiacetic acid prepared by an otherwise identical process in which no seed crystals are introduced.

19. The process as set forth in claim 17 wherein a bed comprising crystallized N-(phosphonomethyl)iminodiacetic acid is formed, the bed having a filtration rate greater than a bed of crystallized N-(phosphonomethyl)iminodiacetic acid prepared by an otherwise identical process in which no seed crystals are introduced.

20. The process as set forth in claim 17 wherein a bed comprising crystallized N-(phosphonomethyl)iminodiacetic acid is formed, the bed having a porosity greater than a bed of crystallized N-(phosphonomethyl)iminodiacetic acid prepared by an otherwise identical process in which no seed crystals are introduced.

21. The process as set forth in claim 17 wherein the yield of crystallized N-(phosphonomethyl)iminodiacetic acid is greater than the yield of crystallized N-(phosphonomethyl)iminodiacetic acid prepared by an otherwise identical process in which no seed crystals are introduced.

22. The process as set forth in claim 17 wherein a bed comprising crystallized N-(phosphonomethyl)iminodiacetic acid is formed, the bed having a lower total impurity concentration on a dry basis than a bed of crystallized N-(phosphonomethyl)iminodiacetic acid prepared by an otherwise identical process in which no seed crystals are introduced.

23. The process as set forth in claims 22 wherein the bed comprising crystallized N-(phosphonomethyl)iminodiacetic acid formed has a chloride content of less than about 5000 ppm by weight on a dry basis.

24. The process as set forth in claim 23 wherein the bed comprising crystallized N-(phosphonomethyl)iminodiacetic acid formed has a chloride content of less than about 3000 ppm by weight on a dry basis.

25. The process as set forth in claim 24 wherein the bed comprising crystallized N-(phosphonomethyl)iminodiacetic acid formed has a chloride content of less than about 1000 ppm by weight on a dry basis.

26. The process as set forth in claim 25 wherein the bed comprising crystallized N-(phosphonomethyl)iminodiacetic acid formed has a chloride content of less than about 250 ppm by weight on a dry basis.

27. The process as set forth in claim 22 wherein the bed comprising crystallized N-(phosphonomethyl)iminodiacetic acid formed has an N-methyl-N-(phosphonomethyl)glycine content of less than about 9,000 ppm by weight on a dry basis.

28. The process as set forth in claim 22 wherein the bed comprising crystallized N-(phosphonomethyl)iminodiacetic acid formed has an N,N-bis(phosphonomethyl)glycine content of less than about 10,000 ppm by weight on a dry basis.

29. The process as set forth in claim 17 wherein a bed comprising crystallized N-(phosphonomethyl)iminodiacetic acid is formed, the bed having a chloride content of less than about 1000 ppm by weight on a dry basis and a permeability of at least about $1 \times 10^{-9}$ cm$^2$.

30. The process as set forth in claim 3 wherein the reaction solution to which the N-(phosphonomethyl)iminodiacetic acid seed crystals are added has a supersaturated concentration of N-(phosphonomethyl)iminodiacetic acid between about $0.5\sigma$ and about $1.5\sigma$.

31. The process as set forth in claim 30 wherein a bed comprising crystallized N-(phosphonomethyl)iminodiacetic acid is formed, the bed having a permeability greater than a bed of crystallized N-(phosphonomethyl)iminodiacetic acid prepared by an otherwise identical process in which no seed crystals are introduced.

32. The process as set forth in claim 30 wherein a bed comprising crystallized N-(phosphonomethyl)iminodiacetic acid is formed, the bed having a filtration rate greater than a bed of crystallized N-(phosphonomethyl)iminodiacetic acid prepared by an otherwise identical process in which no seed crystals are introduced.

33. The process as set forth in claim 30 wherein a bed comprising crystallized N-(phosphonomethyl)iminodiacetic acid is formed, the bed having a porosity greater than a bed of crystallized N-(phosphonomethyl)iminodiacetic acid prepared by an otherwise identical process in which no seed crystals are introduced.

34. The process as set forth in claim 30 wherein the yield of crystallized N-(phosphonomethyl)iminodiacetic acid is greater than the yield of crystallized N-(phosphonomethyl)iminodiacetic acid prepared by an otherwise identical process in which no seed crystals are introduced.

35. The process as set forth in claim 30 wherein a bed comprising crystallized N-(phosphonomethyl)iminodiacetic acid is formed, the bed having a lower total impurity concentration on a dry basis than a bed of crystallized N-(phosphonomethyl)iminodiacetic acid prepared by an otherwise identical process in which no seed crystals are introduced.

36. The process as set forth in claim 35 wherein the bed comprising crystallized N-(phosphonomethyl)iminodiacetic acid formed has a chloride content of less than about 5000 ppm by weight on a dry basis.

37. The process as set forth in claim 36 wherein the bed comprising crystallized N-(phosphonomethyl)iminodiacetic acid formed has a chloride content of less than about 3000 ppm by weight on a dry basis.

38. The process as set forth in claim 37 wherein the bed comprising crystallized N-(phosphonomethyl)iminodiacetic acid formed has a chloride content of less than about 1000 ppm by weight on a dry basis.

39. The process as set forth in claim 38 wherein the bed comprising crystallized N-(phosphonomethyl)iminodiacetic acid formed has a chloride content of less than about 250 ppm by weight on a dry basis.

40. The process as set forth in claims 35 wherein the bed comprising crystallized N-(phosphonomethyl)iminodiacetic acid formed has an N-methyl-N-(phosphonomethyl)glycine content of less than about 9,000 ppm by weight on a dry basis.

41. The process as set forth in claim 35 wherein the bed comprising crystallized N-(phosphonomethyl)iminodiacetic acid formed has an N,N-bis(phosphonomethyl)glycine content of less than about 10,000 ppm by weight on a dry basis.

42. The process as set forth in claim 30 wherein a bed comprising crystallized N-(phosphonomethyl)iminodiacetic acid is formed, the bed having a chloride content of less than about 1000 ppm by weight on a dry basis and a permeability of at least about $1 \times 10^{-9}$ cm$^2$.

43. The process as set forth in claim 1 wherein the alkali metal salt of iminodiacetic acid comprises the disodium salt.

44. The process as set forth in claim 1 wherein the strong mineral acid comprises hydrochloric acid.

45. The process as set forth in claim 1 wherein the source of phosphorous acid comprises phosphorus trichloride.

46. The process as set forth in claim 1 wherein the source of formaldehyde is selected from the group consisting of formaldehyde, formalin and paraformaldehyde.

47. The process as set forth in claim 1 wherein the N-(phosphonomethyl)iminodiacetic acid seed crystals are added to the reaction solution after between about 30% and about 75% of the source of formaldehyde has been combined with the reaction solution.

48. The process as set forth in claim 1 wherein:
   a first portion of the alkali metal salt of iminodiacetic acid is contacted with the strong mineral acid and the source of phosphorous acid in a hydrolysis reaction thereby producing a hydrolyzate comprising phosphorous acid, the strong mineral acid and the salt of the mineral acid and iminodiacetic acid; and
   a second portion of the alkali metal salt of iminodiacetic acid and the source of formaldehyde is contacted with the hydrolyzate in a phosphonomethylation reaction to form the reaction solution comprising N-(phosphonomethyl)iminodiacetic acid.

49. The process as set forth in claim 48 wherein the first portion of the alkali metal salt of iminodiacetic acid comprises from about 55% by weight to about 80% by weight of the total amount of the alkali metal salt of iminodiacetic acid introduced into the process and the second portion of the alkali metal salt of iminodiacetic acid comprises the remainder of the total amount of the alkali metal salt of iminodiacetic acid introduced into the process.

50. The process as set forth in claim 49 wherein the first portion of the alkali metal salt of iminodiacetic acid comprises from about 60% by weight to about 75% by weight of the total amount of the alkali metal salt of iminodiacetic acid introduced into the process.

51. The process as set forth in claim 1 wherein the source of formaldehyde is continually added to the reaction solution over an addition time period.

52. The process as set forth in claim 51 wherein the addition time period is between about 20 minutes and about 180 minutes.

53. The process as set forth in claim 48 wherein a first part of the second portion of the alkali metal salt of iminodiacetic acid and a first portion of the source of formaldehyde are added to the phosphonomethylation reaction over an addition time period, the addition of the alkali metal salt of iminodiacetic acid and the source of formaldehyde to the phosphonomethylation reaction is interrupted, and a second part of the second portion of the alkali metal salt of iminodiacetic acid and a second portion of the source of formaldehyde are added to the phosphonomethylation reaction.

54. The process as set forth in claim 1 wherein a first portion of the source of formaldehyde is added to the reaction solution over a first addition time period at a first addition rate schedule, the source of formaldehyde addition is interrupted, and a second portion of the source of formaldehyde is added to the reaction solution over a second addition time period at a second addition rate schedule.

55. The process as set forth in claim 54 wherein the first addition average rate is greater than the second addition average rate.

56. The process as set forth in claim 1 wherein a first portion of the source of formaldehyde is added to the reaction solution over a first addition time period at a first addition rate schedule and a second portion of the source of formaldehyde is added to the reaction solution over a second addition time period at a second addition rate schedule.

57. The process as set forth in claim 56 wherein the first addition average rate is greater than the second addition average rate.

58. The process as set forth in claim 1 wherein a second portion of an alkali metal salt of iminodiacetic acid, a strong mineral acid, a source of phosphorous acid and a source of formaldehyde are added to the reaction solution to form additional N-(phosphonomethyl)iminodiacetic acid thereby inducing N-(phosphonomethyl)iminodiacetic acid saturation in the reaction solution and crystallization of N-(phosphonomethyl)iminodiacetic acid onto the seed crystals.

59. The process of claim 58 wherein the first portion of the source of formaldehyde is between about 30% and about 75% of the total of the first and the second portions of the source of formaldehyde added to the reaction solution.

60. The process as set forth in claim 58 wherein a first fraction of the first portion of the source of formaldehyde and/or a first fraction of the second portion of the source of formaldehyde is added to the reaction solution over a first fraction addition time period at a first fraction addition rate schedule, the formaldehyde addition is interrupted, and a second fraction of the first portion of the source of formaldehyde and/or a second fraction of the second portion of the source of formaldehyde is added to the reaction solution over a second fraction addition time period at a second fraction addition rate schedule.

61. The process as set forth in claim 60 wherein the first fraction average addition rate is greater than the second fraction average addition rate.

62. The process as set forth in claim 58 wherein a first fraction of the first portion of the source of formaldehyde and/or a first fraction of the second portion of the source of formaldehyde is added to the reaction solution over a first fraction addition time period at a first fraction addition rate schedule, and a second fraction of the first portion of the source of formaldehyde and/or a second fraction of the second portion of the source of formaldehyde is added to the reaction solution over a second fraction addition time period at a second fraction addition rate schedule.

63. The process as set forth in claim 62 wherein the first fraction average addition rate is greater than the second fraction average addition rate.

64. The process as set forth in claim 1 further comprising oxidizing N-(phosphonomethyl)iminodiacetic acid obtained from the N-(phosphonomethyl)iminodiacetic acid crystals to form an N-(phosphonomethyl)glycine product.

65. The process as set forth in claim 64 wherein the N-(phosphonomethyl)glycine product is converted to a salt selected from the group consisting of alkali metal salts, alkanolamine salts, alkyl amine salts and alkyl sulfonium salts of N-(phosphonomethyl)glycine.

66. A process for preparing and crystallizing a product, the process comprising:
  combining one or more product precursor compounds to form a reaction solution;
  reacting the product precursor compound or compounds to form the product;
  adding seed crystals of the product to the reaction solution; and
  inducing a degree of saturation in the reaction solution sufficient to cause crystallization of the product onto the seed crystals, the crystallization driven by chemical reaction that comprises reacting the product precursor compound or compounds to increase the concentration of the product in the reaction solution.

* * * * *